(12) United States Patent
Lee et al.

(10) Patent No.: US 8,980,571 B2
(45) Date of Patent: Mar. 17, 2015

(54) METHOD OF IDENTIFYING A CANDIDATE COMPOUND WHICH MAY INHIBIT α9-NACHR OVEREXPRESSION OR ESTROGEN RECEPTOR-DEPENDENT TRANSCRIPTION IN NICOTINE-DERIVED-COMPOUND-INDUCED BREAST CANCER CELLS

(75) Inventors: Chia-Hwa Lee, Taipei (TW); Ya-Chieh Chang, Taipei (TW); Ching-Shyang Chen, Taipei (TW); Shih-Hsin Tu, Taipei (TW); Ying-Jan Wang, Taipei (TW); Li-Ching Chen, Taipei (TW); Yu-Jia Chang, Taipei (TW); Po-Li Wei, Taipei (TW); Hui-Wen Chang, Taipei (TW); Chien-Hsi Chang, Taipei (TW); Ching-Shui Huang, Taipei (TW); Chih-Hsiung Wu, Taipei (TW); Yuan-Soon Ho, Taipei (TW)

(73) Assignee: Taipei Medical University, Taipei (TW)

( * ) Notice: Subject to any disclaimer, the term of this patent is extended or adjusted under 35 U.S.C. 154(b) by 553 days.

(21) Appl. No.: 13/091,956

(22) Filed: Apr. 21, 2011

(65) Prior Publication Data

US 2012/0270799 A1  Oct. 25, 2012

(51) Int. Cl.
*C12Q 1/68* (2006.01)
*A61K 31/138* (2006.01)
*A61K 31/4196* (2006.01)
*G01N 33/574* (2006.01)
*G01N 33/74* (2006.01)
*G01N 33/94* (2006.01)

(52) U.S. Cl.
CPC ............ *A61K 31/138* (2013.01); *A61K 31/4196* (2013.01); *G01N 33/57415* (2013.01); *G01N 33/743* (2013.01); *G01N 33/944* (2013.01)
USPC ......................................... 435/7.8; 435/6.13

(58) Field of Classification Search
None
See application file for complete search history.

(56) References Cited

FOREIGN PATENT DOCUMENTS

WO    WO 99/11760    *    3/1999

OTHER PUBLICATIONS

C. Kent Osborne, Steroid hormone receptors in breast cancer management, Breast Cancer Research and Treatment, 1998, pp. 227-238, vol. 51.
Rowan T. Chlebowski et al., Breast Cancer after Use of Estrogen plus Progestin in Postmenopausal Women, The New England Journal of Medicine, Feb. 5, 2009, pp. 573-587, vol. 360, No. 6.
Andrzej M. Brzozowski et al., Molecular basis of agonism and antagonism in the oestrogen receptor, Nature, Oct. 16, 1997, pp. 753-758, vol. 389.
Chia-Hwa Lee et al., Overexpression and Activation of the a9-Nictotinic Receptor During Tumorigenesis in Human Breast Epithelial Cells, Journal of the National Cancer Institute, Sep. 8, 2010, pp. 1322-1335, vol. 102, Issue 17.
Joan S Lewis et al., Differential effects of 16a-hydroxyestrone and 2-methoxyestradiol on cyclin D1 involving the transcription factor ATF-2 in MCF-7 breast cancer cells, Journal of Molecular Endocrinology, 2006, pp. 91-105, vol. 34.
Yuan-Soon Ho et al., Dihydrolipoic acid inhibits skin tumor promotion through anti-inflammation and anti-oxidation, Biochemical Pharmacology, 2007, pp. 1786-1795, vol. 73.
Joeri L. Aerts et al., Selection of appropriate control genes to assess expression of tumor antigens using real-time RT-PCR, BioTechniques, 2004, pp. 84,86,88,90-91, vol. 36, No. 1.
Shih-Hsin Tu et al., Increased expression of enolase a in human breast cancer confers tamoxifen resistance in human breast cancer cells, Breast Cancer Res Treat, 2010, pp. 539-553, vol. 121.
Tao Lu et al., Gene regulation and DNA damage in the ageing human brain, Nature, Jun. 24, 2004, pp. 883-891, vol. 429.
Chen Huang et al., Detection of CCND1 amplification using laser capture microdissection coupled with real-time polymerase chain reaction in human esophageal squamous cell carcinoma, Cancer Genetics and Cytogenetics, 2007, pp. 19-25, vol. 175.
Lisa M. McShane et al., Reporting Recommendations for Tumor Marker Prognostic Studies, Journal of Clinical Oncology, Dec. 20, 2006, pp. 9067-9072, vol. 23, No. 36.
Lisa M McShane et al., REporting recommendations for tumor MARKer prognostic studies (REMARK), Nature, Aug. 2005, pp. 416-422, vol. 2, No. 8.
A.M. Pasapera Limon et al., The phosphatidylinositol 3-kinase inhibitor LY294002 binds the estrogen receptor and inhibits 17B-estradiol-induced transcriptional activity of an estrogen sensitive reporter gene, Molecular and Cellular Endocrinology, 2003, pp. 199-202, vol. 200.
Hiroko Yamashita et al., Low phosphorylation of estrogen receptor a (ERa) serine 118 and high phosphorylation of ERa serine 167 improve survival in ER-postitive breast cancer, Endocrine-Related Cancer, 2008, pp. 755-763, vol. 15.
Dietrich Hoffmann et al., Nicotine-derived N-Nitrosamines and Tobacco-related Cancer: Current Status and Future Directions, Cancer Research, Mar. 1985, pp. 935-944, vol. 45.

(Continued)

*Primary Examiner* — Jim Ketter
(74) *Attorney, Agent, or Firm* — WPAT, P.C.; Anthony King; Kay Yang

(57) ABSTRACT

The invention relates to methods of identifying a candidate compound which may inhibit estrogen receptor-dependent transcription or α9-nAChR overexpression and proliferation of nicotine-derived-compound-induced breast cancer cells by using an activating protein 1 (AP1) polypeptide. The invention found that α9-nAChR has an activating protein 1 (AP1)-binding site, that the α9-nAChR promoter is located at the AP1-binding site, and that ERs specifically bind to the α9-nAChR promoter at the AP1-binding site, indicating that ER-induced α9-nAChR up-regulation plays a central role in the response to endogenous (E2) or exogenous (nicotine) stimulation.

4 Claims, 14 Drawing Sheets

(56) References Cited

OTHER PUBLICATIONS

Gundula Risse et al., Asymmetrical recognition of the palindromic AP1 binding site (TRE) by Fos protein complexes, The EMBO Journal, 1989, pp. 3825-3832, vol. 8, No. 12.

Sreeram V. Ramagopalan et al., A ChIP-seq defined genome-wide map of vitamin D receptor binding: Associations with disease and evolution, Genome Research, 2010, pp. 1-9.

Chia-Hwa Lee et al., Crosstalk between nicotine and estrogen-induced estrogen receptor activation induces a9-nicotinic acetylcholine receptor expression in human breast cancer cells, Breast Cancer Res Treat, 2010.

Office Action issued on Sep. 11, 2013 by Taiwan Patent Office for the corresponding Taiwan Patent Application No. 100113408.

English Translation of Office Action issued on Sep. 11, 2013 by Taiwan Patent Office for the corresponding Taiwan Patent Application No. 100113408.

Chang Ya Chieh, "17 beta-estradiol (E2) and Nicotine Can Increase Nicotinic Acetylcholine Receptor alpha9 ( nAChR alpha9 ) Gene Expression Through PI3K/Akt and MAPK Signaling Transduction Pathway in MCF-7 Human Breast Cancer Cells", 2008.

English translation of Chang Ya Chieh, "17 beta-estradiol (E2) and Nicotine Can Increase Nicotinic Acetylcholine Receptor alpha9 ( nAChR alpha9 ) Gene Expression Through PI3K/Akt and MAPK Signaling Transduction Pathway in MCF-7 Human Breast Cancer Cells", 2008.

Kushner PJ, Estrogen receptor pathways to AP-1, Journal of Steroid Biochemistry and Molecular Biology, 2000, vol. 74, pp. 311-317.

* cited by examiner

A

B

A

B

C

A

B

METHOD OF IDENTIFYING A CANDIDATE COMPOUND WHICH MAY INHIBIT α9-NACHR OVEREXPRESSION OR ESTROGEN RECEPTOR-DEPENDENT TRANSCRIPTION IN NICOTINE-DERIVED-COMPOUND-INDUCED BREAST CANCER CELLS

FIELD OF THE INVENTION

The invention relates to methods of identifying a candidate compound which may inhibit estrogen receptor-dependent transcription or α9-nAChR overexpression and proliferation of nicotine-derived-compound-induced breast cancer cells. Particularly, an activating protein 1 (AP1) polypeptide, 1α,25 (OH)$_2$D$_3$ receptor (VDR) polypeptide, API polynucleotide or VDR polynucleotide is used in the methods.

BACKGROUND OF THE INVENTION

Breast cancer is the second leading cause of cancer-related death among women in the USA. Tobacco, a substance that contains human carcinogens, may contribute to the risk for breast cancer development in women. Large cohort epidemiological studies that were performed in the USA and Japan indicate that the risk for breast cancer is associated with both active and passive smoking. Cigarette smoke is a complex mixture of over 4,000 chemical constituents. On average, roughly 1.0 mg (range of 0.3-2.0 mg) of nicotine is absorbed systemically while smoking a cigarette, and studies performed using $^{14}$C-nicotine have shown that 80-90% of the inhaled nicotine is absorbed by the body. Nicotine concentrations in the plasma can reach levels of approximately 15 ng/ml immediately after smoking and even higher levels in the saliva and gastric juice (>1300 and >800 ng/ml, respectively). Previous studies using a soft agar transforming assay and a xenografted nude mouse animal model have shown that non-cancerous human breast epithelial (MCF-10A) cells are transformed by either a cigarette smoke condensate or the tobacco-specific carcinogen 4-(methylnitrosamino)-1-(3-pyridyl)-1-butanone (NNK). In vivo studies have demonstrated that nicotine promotes the growth of solid tumors, which suggests that it might contribute to the progression of cell proliferation, invasion, and angiogenesis in tumors. Such results imply that nicotinic alteration of normal breast epithelial cells may also contribute to breast cancer tumorigenesis.

Among all body tissues, human neuronal tissues have been reported to exhibit the most abundant expression of nicotinic acetylcholine receptor (nAChR) subunits. These receptors are composed of either heteropentamers that comprise a combination of a (α1-α6) and b (β2-β4) subunits or homopentamers consisting of α7-α10 subunits that are symmetrically arranged around a central ion pore. The physiological ligand of nAChRs is acetylcholine; however, some tobacco components, including nicotine and its active metabolites, such as the nitrosamines N'-nitrosonornicotine and NNK, are high-affinity agonists of nAChRs. Recent studies have shown that nAChRs can accelerate cell proliferation, tumor invasion, and angiogenesis in addition to conferring resistance against apoptosis.

Most mammary carcinomas contain estrogen receptors (ER), which are important factors for diagnosis and prognosis of breast cancer, and for determining therapeutic choices (Osborne, 1998, Breast Cancer Res. Treat., 51, 227). Estrogens are direct mitogens for hormone-responsive human breast cancer cells, where they promote cell cycle progression and induce the transcriptional activation of "immediate early" and cyclin genes. The relationships between breast cancer formation, estrogen receptor (ER) (which mediates both hormone-induced gene transcription and anti-estrogen action against breast cancer), and ER ligands (such as estrogen, E2) have been discussed in a recent article (Chlebowski, R. T., Kuller, L. H., Prentice, R. L., Stefanick, M. L., Manson, J. E., Gass, M., Aragaki, A. K., Ockene, J. K., Lane, D. S., Sarto, G. E., et al. 2009. *Breast cancer after use of estrogen plus progestin in postmenopausal women. N Engl J Med* 360:573-587). E2, a group of steroid hormones, act primarily by regulating gene expression after binding to the ER, a nuclear ligand-activated transcription factor. The binding of an agonist (E2) induces a conformational change in the ER that enables it to homodimerize. This dimer is then translocated to the nucleus where it enhances gene transcription. ER activity may modulate the rate of transcription initiation by interacting with the basal transcriptional machinery and by changing the chromatin arrangement at the promoters of its target genes via the recruitment of a variety of coactivators. This ER/coactivator complex activates DNA transcription by stimulating E2 responsive elements (Brzozowski, A. M., Pike, A. C., Dauter, Z., Hubbard, R. E., Bonn, T., Engstrom, O., Ohman, L., Greene, G. L., Gustafsson, J. A., and Carlquist, M. 1997. *Molecular basis of agonism and antagonism in the oestrogen receptor. Nature* 389:753-758). Additional target molecules that are involved in ER-mediated signaling pathways in breast cancer formation, however, remain to be identified.

Smoking and hormones are two important etiological factors involved in breast cancer formation (Daniell, H. W. 1980. *Estrogen receptors, breast cancer, and smoking. N Engl J Med* 302:1478). A recent study demonstrated that α9-nAChR expression plays a decisive role in smoking-induced breast cancer formation (Lee, C. H., Huang, C. S., Chen, C. S., Tu, S. H., Wang, Y. J., Chang, Y. J., Tam, K. W., Wei, P. L., Cheng, T. C., Chu, J. S., et al. 2010. *Overexpression and activation of the alpha9-nicotinic receptor during tumorigenesis in human breast epithelial cells. J Natl Cancer Inst* 102:1322-1335).

Therefore, there is a need to screen compounds that inhibit the α9-nAChR overexpression so as to treat and prevent nicotine-derived-compound-induced breast cancer.

DETAILED DESCRIPTION OF THE INVENTION

Figure 1:
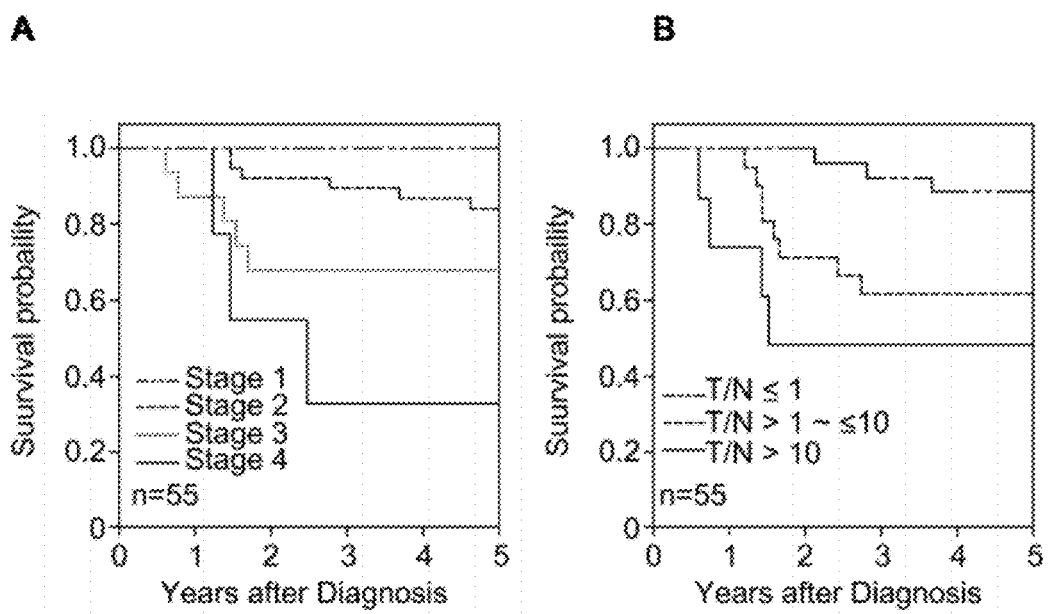
FIG. 1 shows Kaplan-Meier estimates of the 5-year disease-specific survival of 55 patients. The patients were grouped according to A) the pathological stage of the tumor and B) α9-nAChR mRNA expression as determined by real-time PCR analysis. The population figures of at-risk patients in each group are listed in Table 1.

The inventors surprisingly found that nicotine and estrogen both induce α9-nAChR expression in breast cancer cells, so inhibition of activation of estrogen receptors is able to inhibit overexpression of α9-nAChR and proliferation of nicotine-derived-compound-induced breast cancer cells. Interestingly, estrogen receptors (ERs) are activated by treatment with either nicotine or estrogen. The invention first identified that α9-nAChR has an activating protein 1 (AP1)-binding site and a 1α,25(OH)$_2$D$_3$ receptor (VDR) binding site and the α9-nAChR promoters are located at both the AP1-binding site and VDR binding site. Promoter activity assay shows that ERs specifically bind to the α9-nAChR promoter at the AP1-binding site and VDR binding site, indicating that ER-induced α9-nAChR up-regulation plays a central role in the response to endogenous (E2) or exogenous (nicotine) stimulation, which confers the carcinogenic effects observed in breast tumor formation.

The use of the word "a" or "an" when used in conjunction with the term "comprising" in the claims and/or the specification may mean "one," but is also consistent with the meaning of "one or more," "at least one," and "one or more than one."

The term "overexpression" refers to the level of expression in cells or organisms that exceeds levels of expression in normal cells or organisms.

The "breast cancer" as used herein denotes cancer which originates in the breast. In a specific embodiment, the breast cancer spreads to other organs, such as lymph nodes. In a specific embodiment, the breast cancer is invasive and may be metastatic.

The "cancer" as used herein denotes a new growth of tissue comprising uncontrolled and progressive multiplication. In a specific embodiment, upon a natural course the cancer is fatal. In specific embodiments, the cancer is invasive, metastatic, and/or anaplastic (loss of differentiation and of orientation to one another and to their axial framework).

The "candidate compound" as used herein is meant a chemical, be it naturally occurring or artificially derived. Candidate compounds may include, for example, peptides, polypeptides, synthetic organic molecules, naturally occurring organic molecules, nucleic acid molecules, peptide nucleic acid molecules, and components and derivatives thereof.

The "diagnosis" as used herein refers to the identification of a molecular or pathological state, disease or condition, such as the identification of a molecular subtype of head and neck cancer, colon cancer, or other type of cancer.

The term "sample" as used herein refers to a biological sample, such as, for example, tissue or fluid isolated from a subject (including without limitation plasma, serum, cerebrospinal fluid, lymph, tears, saliva and tissue sections) or from in vitro cell culture constituents.

The term "prognosis" used herein refers to the prediction of the likelihood of cancer-attributable death or progression, including recurrence, metastatic spread, and drug resistance, of a neoplastic disease, such as breast cancer. "Good prognosis" denotes that a patient is expected to have no distant metastases of a breast tumor within five years of initial diagnosis of breast cancer. "Poor prognosis" denotes that a patient is expected to have distant metastases of a breast tumor within five years of initial diagnosis of breast cancer.

The term "sample" as used herein refers to a biological sample, such as, for example, tissue or fluid isolated from a subject (including without limitation plasma, serum, cerebrospinal fluid, lymph, tears, saliva and tissue sections) or from in vitro cell culture constituents.

In one aspect, the invention provides a method of inhibiting overexpression of α9-nAChR or estrogen receptor-dependent transcription in nicotine-derived-compound-induced breast cancer cells, comprising administering an effective amount of an anti-estrogen drug to the mammal. Preferably, the anti-estrogen drug includes, but is not limited to, tamoxifen, femara, and arimidex.

In another aspect, the invention provides a method of identifying a candidate compound which may inhibit overexpression of α9-nAChR or estrogen receptor-dependent transcription in nicotine-derived-compound-induced breast cancer cells, comprising contacting the compound with the AP1 polypeptide or VDR polypeptide and determining whether the compound binds to the polypeptide, wherein binding of the compound to the polypeptide indicates that the compound may inhibit overexpression of α9-nAChR or estrogen receptor-dependent transcription in nicotine-derived-compound-induced breast cancer cells.

In another aspect, the invention provides a method of identifying a candidate compound which may inhibit overexpression of α9-nAChR and proliferation or estrogen receptor-dependent transcription in nicotine-derived-compound-induced breast cancer cells, comprising contacting the compound with the AP1 polynucleotide or VDR polynucleotide and determining whether the compound binds to the polynucleotide, wherein binding of the compound to the polynucleotide indicates that the compound may inhibit overexpression of α9-nAChR or estrogen receptor-dependent transcription in nicotine-derived-compound-induced breast cancer cells.

In a further aspect, the invention provides a method of identifying a candidate compound which may inhibit overexpression of α9-nAChR or estrogen receptor-dependent transcription in nicotine-derived-compound-induced breast cancer cells, comprising contacting the AP1 polypeptide or VDR polypeptide and an estrogen receptor polypeptide with the compound and determining the ability of the compound to interfere with the binding of the estrogen receptor polypeptide with the AP1 polypeptide or VDR polypeptide, wherein interference of the binding of the estrogen receptor polypeptide and the AP1 polypeptide or VDR polypeptide indicates the compound may inhibit overexpression of α9-nAChR or estrogen receptor-dependent transcription in nicotine-derived-compound-induced breast cancer cells.

It is known in the art that nicotine is not a complete carcinogen and nitrosation of nicotine gives NNN ("N'-nitrosonomicotine") by cleavage of the N—CH$_3$ bond with loss of formaldehyde or yields NNK ("4-(methylnitros-amino}-t-(3-pyridyl)-1-butanone" (the origin of the term NNK is "nicotine-derived nitrosaminoketone") or NNA ("4-fmethylnitrosamino)-4-{3-pyridyl)-butanal") by cleavage of either the 2'-N or 5'-N bond, respectively (*Cancer Research* 45, 935-944, March 1985, which incorporated herein by reference in its entirety). The nicotine derived compounds are carcinogens.

The invention found that nicotine-induced ER-responsive elements are located at the AP1 site (SEQ ID NOs:1 and 2, nnTGAC(or G)nnnnn, n can be any one of A, T, C and G) and the VDR site (SEQ ID NOs 3 and 4, nnnnnnnnGAGG(or T)nnn, n can be any one of A, T, C and G). Screening methods to identify candidate compounds which inhibit estrogen-dependent transcription, AP1 expression or VDR expression, or an AP1/ER or VDR/ER interaction in nicotine-derived-compound-induced breast cancer cells (and as a result, induction of estrogen receptor-dependent transcription and overexpression of α9-nAChR in nicotine-derived-compound-induced breast cancer cells and proliferation of the cells) are within the scope of the invention. For example, a method of identifying a candidate compound which inhibits ER-dependent transcription is carried out by contacting the compound with an AP1 polypeptide or VDR polypeptide and determining whether the compound binds to the polypeptide. Binding of the compound to the polypeptide indicates that the compound inhibits ER-dependent transcription, and in turn, overexpression of α9-nAChR and proliferation of nicotine-derived-compound-induced breast cancer cells. Preferably, the AP1 polypeptide is encoded by a polynucleotide comprising a sequence of nnTGAC(or G)nnnnn. More preferably, the AP1 polypeptide is encoded by a polynucleotide comprising a sequence selecting from the group consisting of ccTGACtgaga (SEQ ID NO:5), naTGAGtcagn (SEQ ID NO:6), ntTGAGtcagn (SEQ ID NO:7), ngTGAGtcagn (SEQ ID NO:8), naTGAGtcacn (SEQ ID NO:9), naTGAGtcagn (SEQ ID NO:10) and naTGAGtcaan (SEQ ID NO:11), such as that described in Gundula Risse, et al., The EMBO Journal 8(12), p. 3825-3832, 1989, and is herein incorporated in its entity by reference. Preferably, the VDR polypeptide is encoded by a polynucleotide comprising a sequence of nnnnnnnnGAGG (orT)nnn. More preferably, the VDR polypeptide is encoded by a polynucleotide comprising a sequence selecting from the group consisting of aggggaggGAGGgca (SEQ ID NO:12), aggggaggGAGGtca (SEQ ID NO:13), agggtcaaGAGGtca (SEQ ID NO:14), gggtggaaGAGGtca (SEQ ID NO:15), aaggtcaaGAGTtca (SEQ ID NO:16) and gggtggaaGAGTgtg (SEQ ID NO:17), such as that described in Sreeram V. Ramagopalan et al., Genome Research, published online Aug. 24, 2010, and is herein incorporated in its entity by reference. Alternatively, the method is carried out by contacting the compound with the AP1 polynucleotide or VDR polynucleotide and determining whether the compound binds to the polynucleotide. Alternatively, the method is carried out by contacting the compound with an AP1 polypeptide or VDR polypeptide and an ER polypeptide and determining the ability of the compound to interfere with the binding of the ER polypeptide with the AP1 polypeptide or VDR polypeptide. A compound which interferes with an AP1/ER or VDR/ER interaction inhibits ER-dependent transcription.

The compounds identified by the methods of the invention can be formulated with one or more acceptable carriers, excipients, or diluents for administration. Pharmaceutically acceptable carriers for therapeutic use are well known in the pharmaceutical art, and are described, for example, in Remington's Pharmaceutical Sciences, Gennaro, A R, ed., 20th edition, 2000: Williams and Wilkins Pa., USA, which is incorporated herein by reference for all purposes. While any known suitable carrier may be employed in a pharmaceutical formulation of this invention, the type of carrier will vary depending on the mode of administration and whether a sustained release is desired. Routes of delivery may include oral, inhaled, buccal, parenteral, and transdermal routes, as well as novel delivery systems such as the protective liposomes for oral delivery of peptides.

Diagnostic methods to identify an aberrantly proliferating cell, e.g., a nicotine-derived-compound-induced breast cancer cell are also included in the invention. For example, a method of detecting an aberrantly proliferating cell in a sample suspicious of nicotine-derived-compound-induced breast cancer is carried out by determining the level of AP1 or VDR gene expression in the sample. An increase in the level of gene expression compared to that in a normal control tissue indicates the presence of an aberrantly proliferating cell. AP1 or VDR gene expression is measured using an AP1 or VDR gene-specific polynucleotides probe, e.g. in a Northern assay or polymerase chain reaction (PCR)-based assay, to detect AP1 or VDR mRNA transcripts. AP1 or VDR gene expression can also be measured using an antibody specific for an AP1 or VDR gene product, e.g., by immunohistochemistry or Western blotting.

Aberrantly proliferating cells as mentioned above, e.g., cancer cells, in a sample may be detected by determining the number of cellular copies of an AP1 or VDR gene in the tissue. An increase in the number of gene copies in a cell of a patient-derived tissue compared to that in normal control tissue indicates the presence of a cancer. An increase in copy number compared to the normal diploid copy number indicates that the tissue sample contains nicotine-derived-compound-induced breast cancers. AP1 or VDR copy number is measured by fluorescent in situ hybridization (FISH), Southern hybridization techniques, and other methods well known in the art.

According to the invention, the sample is a tissue or fluid isolated from a subject including without limitation plasma, serum, cerebrospinal fluid, lymph, tears, saliva and tissue sections.

The invention also includes methods of treating a mammal suffering from nicotine-derived-compound-induced breast cancer, e.g., a human patient. For example, a method of reducing proliferation of a nicotine-derived-compound-induced breast cancer cell in a mammal is carried out by administering to the mammal a compound which inhibits expression of AP1 or VDR. The compound reduces transcription of AP1- or VDR-encoding DNA in the cell. Alternatively, the compound reduces translation of an AP1 or VDR mRNA into an AP1 or VDR gene product in the cell. For example, translation of AP1 or VDR mRNA into an AP1 or VDR gene product is inhibited by contacting the mRNA with antisense polynucleotides complementary to the AP1 or VDR mRNA.

A method of inhibiting ER-dependent transcription in a nicotine-derived-compound-induced breast cancer cell is carried out by administering an effective amount of an AP1 or VDR polypeptide or a peptide mimetic thereof to the mammal. Preferably, the polypeptide inhibits an AP1/ER or VDR/ER interaction. By binding to ER, such a polypeptide inhibits binding of AP1 or VDR to ER, thereby inhibiting ER-dependent transcription in a nicotine-derived-compound-induced breast cancer cell.

In another further aspect, the invention provides a kit for identifying a candidate compound which may inhibit overexpression of α9-nAChR and proliferation of nicotine-derived-compound-induced breast cancer cells, comprising a labeled AP1 or VDR polypeptide or a labeled AP1 or VDR polynucleotide. Any detectable label known in the art can be used. For example, a radio-isotope label, an enzyme label, magnetic bead or a fluorescent label can be used. Kits made according to the invention include assays for detecting the label. These can include all or some of the materials needed to conduct the assays such as reagents and instructions.

EXAMPLE

The following experimental examples are provided in order to demonstrate and further illustrate various aspects of certain embodiments of the present invention and are not to be construed as limiting the scope thereof. In the experimental disclosure which follows, the following materials and methods are used:

Materials and Methods

Cell Culture and Patient Samples

All of the human breast tumor samples (n=339) analyzed in this study were obtained as anonymous specimens from the Taipei Medical University Hospital and Cathay General Hospital, Taipei, according to a protocol approved by the Institutional Review Board (P950012). A histological evaluation revealed that all of the patient samples comprised >80% tumor tissue. Immunohistochemical staining-analysis of α9-nicotinic acetylcholine receptors (nAChRs) and p-c-Jun (Ser$^{73}$) was performed using frozen sections from human primary breast tumors. Human mammary gland epithelial adenocarcinomas (MCF-7, MDA-MB-231) were obtained from the American Type Culture collection (ATCC numbers HTB 22 and HTB 26, respectively). MCF-7 and MDA-MB-231 cells were grown and routinely maintained in Dulbecco's Modified Eagle's Medium (DMEM)/F12 supplemented with 10% (v/v) fetal bovine serum (FBS, Biological Industries, Israel), 2 mM L-glutamine, 100 units/ml penicillin, and 100 mg/ml streptomycin. The cells were incubated in a 37° C. incubator with 5.0% CO2. Cell growth, proliferation, and viability were determined using a 3-(4,5-dimethylthiazol-2-yl)-2,5-diphenyltetrazolium (MTT) assay. Nicotine and estrogen (E2) were purchased from Sigma-Aldrich (St. Louis, Mo.). Aqueous stock solutions of 10 μM nicotine and 10 nM E2 were prepared in sterile water and dimethyl sulfoxide (DMSO), respectively.

For the kinase competition assays, the cells were treated with either 10 μM Ly294002, 25 μM PD98059, or 25 μM SP600125 (all from Tocris Cookson Inc., Ellisville, USA) before the treatment with nicotine or E2. All of the cell lines were grown in phenol red-free DMEM for 7 days before the experiments (Lewis, J. S., Thomas, T. J., Pestell, R. G., Albanese, C., Gallo, M. A., and Thomas, T. 2005. *Differential effects of 16alpha-hydroxyestrone and 2-methoxyestradiol on cyclin D1 involving the transcription factor ATF-2 in MCF-7 breast cancer cells. J Mol* Endocrinol 34:91-105). The DMEM medium used for these experiments contained 10% FBS that had been pretreated with dextran-coated charcoal (0.5% Norit A and 0.05% Dextran T-70) to avoid the effects of serum-derived estrogenic compounds.

Protein Extraction, Immunoblotting, and Antibodies

Cell extracts were prepared as previously in Ho, Y. S., Lai, C. S., Liu, H. I., Ho, S. Y., Tai, C., Pan, M. H., and Wang, Y. J. 2007. *Dihydrolipoic acid inhibits skin tumor promotion through anti-inflammation and anti-oxidation. Biochem Pharmacol* 73:1786-1795. Fifty micrograms of protein from each sample were resolved by 12% SDS-polyacrylamide gel electrophoresis, transferred to PVDF and analyzed by western blotting. The antibodies employed for the western blotting analysis were purchased from the following vendors: anti-Akt, anti-JNK, anti-phospho JNK, anti-estrogen receptor a (anti-ERα), anti-c-Fos, anti-ERK1/2, anti-phospho ERK1/2, and protein A/G agarose beads were purchased from Santa Cruz Biotechnology (Santa Cruz, Calif., USA); anti-GAPDH, anti-α9-nAChR, and anti-phospho ERα (Ser$^{167}$) antibodies were obtained from ABcam (Cambridge, UK); anti-phospho Akt (Ser$^{473}$, Thr$^{308}$), anti-phospho c-Jun (Ser$^{73}$), anti-phospho ERα (Ser$^{118}$), and anti-phospho ERα (Ser$^{104/106}$) antibodies were purchased from Cell Signaling Technology (Danvers, Mass.). Immunodetection was performed by probing membranes with the appropriate dilutions of specific primary antibodies at room temperature for 2 h. The membranes were then incubated at room temperature for 1 h with either alkaline phosphatase-coupled anti-mouse or anti-rabbit secondary antibodies that were purchased from Santa Cruz Biotechnology. The specific protein complexes were identified by incubating the membranes with colorigenic substrates (nitroblue tetrazolium and 5-bromo-4-chloro-3indolyl-phosphate; KPL, Inc., Gaithersburg, Md., USA). In each experiment, the membranes were also probed with an anti-GAPDH antibody as a protein loading control.

Reverse-Transcription PCR (RT-PCR) and Real-Time PCR Analysis

Total RNA was isolated from the acquired human cell lines using TRIzol (Invitrogen, Carlsbad, Calif.) according to the manufacturer's suggested protocol. Primers specific for the α9-nAChR subunit (forward: 5'-gtccagggtcttgtttgt-3 (SEQ ID NO:18)' and reverse: 5'-atccgctcttgctatgat-3 (SEQ ID NO:19)') were synthesized by MB Mission BioTech (Taipei, Taiwan). The PCR amplicons were analyzed in 1.2% agarose gels (Amresco, Inc, Solon, Ohio, USA) that were stained with ethidium bromide. Because real-time RT-PCR is a powerful tool for the analysis of gene expression, the data were analyzed using b-glucuronidase (GUS) (forward: 5'-agtgttccct-gctagaatagatg-3 (SEQ ID NO:20)' and reverse: 5'-aaacagc-ccgtttacttgag-3'(SEQ ID NO:21)), which has been reported to be an ideal control gene with low variability (Aerts, J. L., Gonzales, M. I., and Topalian, S. L. 2004. *Selection of appropriate control genes to assess expression of tumor antigens using real-time RT-PCR. Biotechniques* 36:84-86, 88, 90-81), as a control to normalize the expression of the α9-nAChR gene. For the real-time PCR analysis, a LightCycler thermocycler (Roche Molecular Biochemicals, Mannheim, Germany) was used. The α9-nAChR mRNA fluorescence intensity was measured and normalized to GUS expression levels using the built-in Roche LightCycler software (version 4).

Plasmid Construction

All of the α9-nAChR promoter-luciferase gene fusions were constructed using a pGL3-Basic vector (Promega), and suitable α9 promoter fragments were introduced into the polylinker region of the vector, upstream of the luciferase gene. These constructs were defined as pGL3(α9-nAChR). The fragments were generated using restriction enzymes and were either cloned directly into a pGL3-Basic vector or first subcloned in a pBluescript vector and then transferred into a pGL3-Basic vector. Deletion analysis of the most promoter-proximal region was performed by generating either the appropriate restriction enzyme fragments or PCR fragments using full-length α9-nAChR sense (−995) and antisense (−1) oligonucleotide primers (ctgatttggtcagcctttga (SEQ ID NO:22) and cttttcctgagcctctat (SEQ ID NO:23), respectively) that were designed to anneal to the pGL3-Basic vector downstream of the transcription initiation site.

Luciferase Activity Assay

MCF-7 cells were plated in six-well plates and incubated overnight. The following day, the cells were transiently cotransfected with 2 µg of pGL3 (α9-nAChR) promoter plasmid and 500 ng of RLTK plasmid (Promega, Madison, Wis.) using a MP-100 microporator (Digital Bio, Seoul, Korea) according to the manufacturer's instructions. After a 24-h incubation, the medium was replaced with culture medium containing either 10 or 0.1% FBS with or without nicotine and E2. Twenty-four hours later, the cells were lysed with 19 Reporter Lysis Buffer (Promega, Madison, Wis.) and stored at −20° C. overnight. Luciferase activity was then determined by mixing 50 ll of the cell lysate and 50 µl of the Luciferase Assay Reagent (Promega). The total luciferase light units were quantified using a HIDEX Chameleon Microplate Reader. The relative luciferase activity was normalized to that of renilla luciferase in the same cell lysates. Each luciferase assay experiment was performed three times. In this study, the luciferase activity observed in cells transfected with the empty vector was defined as a one-fold change (i.e., basal level). The α9-nAChR promoter serial deletion plasmids were synthesized by PCR using the following primers: forward primers −995 (ctgatttggtcagcctttga) (SEQ ID NO:24), −536 (ctggagatcatagaaccgtg) (SEQ ID NO:25), −260 (acaa-cagcactgttggacct) (SEQ ID NO:26), −139 (atgcaatgcaagcct-gagct) (SEQ ID NO:27), and −41 (gctgcctgactgagacttta) (SEQ ID NO:28); and reverse primers −1 (cttttcctgagcctc-tata) (SEQ ID NO:29), −241 (aggtccaacagtgctgttgt) (SEQ ID NO:30), and −22 (taaagtctcagtcaggcagc) (SEQ ID NO:31).

Chromatin Immunoprecipitation (ChIP) Assay

ChIP assays using the cultured cells were performed as described in Tu, S. H., Chang, C. C., Chen, C. S., Tam, K. W, Wang, Y. J., Lee, C. H., Lin, H. W, Cheng, T. C., Huang, C. S., Chu, J. S., et al. 2009. *Increased expression of enolase alpha in human breast cancer confers tamoxifen resistance in human breast cancer cells. Breast Cancer Res Treat*. In brief, after treatment of the cells with various doses of nicotine or E2 for varying periods, the cells were fixed with a final concentration of 1% formaldehyde by its direct addition to the cell culture media at 25° C. for 15 min. The crosslinking reaction was stopped by the addition of 0.125 M glycine for 5 min, and then the cells were collected in a new eppendorf tube. The cell lysate was sonicated three times using 10-s bursts to yield input DNA that was enriched for fragments of approximately 1000 bp in size. ChIP assays were also performed using clinical tissue samples as described in Lu, T., Pan, Y., Kao, S. Y., Li, C., Kohane, I., Chan, J., and Yankner, B. A. 2004. *Gene regulation and DNA damage in the ageing human brain. Nature* 429:883-891. In brief, the samples were thawed in 500 µl of PBS containing protease inhibitors and homogenized three times on ice using a PRO 200 homogenizer (PRO Scientific Inc., Monroe, Conn.) at setting 3 (18000 rpm). After a mild centrifugation (1200 rpm) for 10 min, the samples were fixed with a final concentration of 1% formaldehyde solution at 25° C. for 15 min.

ERα and p-c-Jun (Ser[73]) antibodies were used for the immunoprecipitation reactions. The α9-nAChR promoter was detected by targeting three different regions from −260, −536 and −995 to −1 by PCR (the sequences of the primers used are listed above). The pS2 promoter region was amplified from the −7 to −426 positions by PCR using a forward primer (ctctctgctccaaaggcga) (SEQ ID NO:32) and a reverse primer (tgagccactgttgtcacg) (SEQ ID NO:33). The PCR products were then detected by agarose gel electrophoresis.

Laser-Capture Microdissection (LCM)

Sections stained with hematoxylin/eosin (H.E.) were subjected to LCM using a PixCell IIe system (Arcturus Engineering, Mountain View, Calif.) (Huang, C., Yang, L., Li, Z., Yang, J., Zhao, J., Dehui, X., Liu, L., Wang, Q., and Song, T. 2007. *Detection of CCND1 amplification using laser capture microdissection coupled with real-time polymerase chain reaction in human esophageal squamous cell carcinoma. Cancer Genet Cytogenet* 175:19-25). The parameters used for LCM included a laser diameter of 7.5 μm and a laser power of 48-65 mW. For each specimen, 15,000 laser pulse discharges were used to capture 10,000 morphologically normal epithelial cells or malignant cells. Each population was analyzed visually using a microscope to ensure that the captured cells were homogeneous. After the cells were captured, total RNA was isolated according to the manufacturer's protocols. From the patient cohort, 12 tumor cell samples were obtained (ER+ and ER−, n=6 per group). The α9-nAChR mRNA expression levels in the laser-capture microdissected cells were assessed by real-time PCR. The data obtained in these experiments represent the mean fold ratios determined in tumor/normal-paired samples from LCM-dissected cells with different clinical ER status criteria. Comparisons between the ER+ and ER-tissues were performed, and the data were analyzed using the Student's t-test. All of the presented P-values are two-sided.

Statistical Methods

In accordance with the REMARK criteria for tumor marker studies described in previous reports (McShane, L. M., Altman, D. G., Sauerbrei, W., Taube, S. E., Gion, M., and Clark, G. M. 2005. *Reporting recommendations for tumor marker prognostic studies (REMARK). J Natl Cancer Inst* 97:1180-1184; McShane, L. M., Altman, D. G., Sauerbrei, W., Taube, S. E., Gion, M., and Clark, G. M. 2006. Reporting recommendations for tumor MARKer prognostic studies (REMARK). *Breast Cancer Res Treat* 100:229-235), all of the data are expressed as the mean±SD, and a univariate analysis was used to compare the α9-nAChR mRNA expression fold ratios detected in tumor/normal-paired samples from surgical-dissected cells, which were compared according to age, 5-year survival, ER status, PR status, Her2/Neu expression, tumor size, nodal status, disease stage, chemotherapy, radiotherapy, tamoxifen, and herceptin usage. Differences in the tumor cell luciferase activity assays were analyzed using the Kruskal-Wallis (nonparametric) test. Kaplan-Meier curves and the log-rank test were used to evaluate differences in the 5 year overall survival rates. All the statistical comparisons were performed using SigmaPlot graphing software (San Jose, Calif.) and the Statistical Package for the Social Sciences v. 11.0.0 (SPSS, Chicago, Ill.). A P-value<0.05 was considered statistically significant, and all of the statistical tests were two-sided.

Example 1

Expression of α9-nAChR in Human Breast Tumor Tissues and 5-Year Disease-Specific Survival Rate In a previous study, the α9-nAChR subunit was important for nicotine-induced breast cancer cell formation (Lee, C. H., Huang, C. S., Chen, C. S., Tu, S. H., Wang, Y. J., Chang, Y. J., Tam, K. W, Wei, P. L., Cheng, T. C., Chu, J. S., et al. 2010. *Overexpression and activation of the alpha9-nicotinic receptor during tumorigenesis in human breast epithelial cells. J Natl Cancer Inst* 102:1322-1335). The α9-nAChR subunit expression levels in 339 tumors versus normal-paired tissue samples were determined by real-time PCR analysis and correlated with clinical parameters (Table 1).

TABLE 1

Results of Analysis of Prognostic Factors and α9-nAchR Expression.

| Factors | No. of Patients | α9-nAchR N > T §mean ± se | P Value | α9-nAchR T > N §mean ± se | P Value |
|---|---|---|---|---|---|
| Age | | | 0.235 | | 0.97 |
| <50yr | 139 | 3.4 ± 0.5 | | 9.0 ± 2.7 | |
| ≥50yr | 200 | 3.6 ± 0.5 | | 9.13 ± 2.6 | |
| Size of tumor | | | .609 | | .174 |
| T1 | 151 | 3.7 ± 1.3 | | 5.1 ± 2.1 | |
| T2 | 155 | 3.0 ± 1.6 | | 8.7 ± 2.6 | |
| T3 | 19 | 2.1 ± 0.6 | | 9.9 ± 5.3 | |
| T4 | 7 | 59.8, n = 1 | | 4.4, n = 1 | |
| Nodal status | | | 0.922 | | .222 |
| N0 | 171 | 4.4 ± 0.6 | | 8.7 ± 2.8 | |
| N1 | 88 | 2.6 ± 0.3 | | 8.5 ± 3.4 | |
| N2 | 39 | 1.6 ± 0.3 | | 11.8 ± 6.1 | |
| N3 | 34 | 2.1 ± 0.9 | | 7.3 ± 3.4 | |
| Stage of disease | | | .928 | | .031* |
| I | 95 | 3.7 ± 1.3 | | 3.1 ± 2.6 | |
| II | 157 | 3.0 ± 0.3 | | 6.9 ± 3.1 | |
| III | 69 | 2.1 ± 0.4 | | 10.3 ± 6.6 | |
| IV | 8 | 18.0, n = 1 | | 25.2 ± 16.2 | |
| ER status | | | .475 | | .045* |
| Negative | 106 | 2.8 ± 0.3 | | 6.7 ± 2.3 | |
| Positive | 224 | 3.7 ± 0.4 | | 11.0 ± 3 | |
| PR status | | | .9 | | .16 |
| Negative | 156 | 3.6 ± 0.5 | | 8.7 ± 2.9 | |
| Positive | 170 | 2.8 ± 0.3 | | 9.2 ± 2.8 | |
| Her-2 status | | | .161 | | .023* |
| Negative | 172 | 2.7 ± 0.3 | | 7.7 ± 2.7 | |
| Positive | 139 | 3.1 ± 0.6 | | 10.5 ± 2.7 | |
| 5-year survival | | | .131 | | .05* |
| Alive | 39 | 3.2 ± 0.3 | | 9.2 ± 2.4 | |
| Dead | 16 | 1.6 ± 0.5 | | 15.2 ± 3.1 | |
| Chemotherapy | | | .759 | | .679 |
| No | 109 | 3.7 ± 0.5 | | 10.2 ± 3.6 | |
| Yes | 223 | 3.5 ± 0.5 | | 8.5 ± 2.2 | |
| Radiotherapy | | | .03* | | .4 |
| No | 245 | 4.1 ± 0.3 | | 10 ± 2.4 | |
| Yes | 87 | 2.7 ± 0.4 | | 5.9 ± 1.6 | |
| Tamoxifen | | | .046* | | .915 |
| No | 136 | 4.5 ± 0.6 | | 9.4 ± 3 | |
| Yes | 196 | 3 ± 0.4 | | 8.9 ± 2.4 | |
| Herceptin | | | .131 | | .268 |
| No | 295 | 3.7 ± 0.4 | | 9.9 ± 2.1 | |
| Yes | 37 | 3.2 ± 1.1 | | 3.8 ± 0.6 | |

*Fold ratios of a9-nAChR mRNA expression were determined in normal/tumor or tumor/normal paired samples. Data were analyzed using univariate analyses. A P-value <0.05 was considered as statistically significant. All P-values are two-sided.
§mean: average fold ratio of α9-nAChR mRNA expression in each group.

It was found that higher α9-nAChR expression levels were associated with significant differences in the disease stage (overall, P=0.031), ER status (ER+ versus ER−, P=0.045), Her2/neu status (Her2/neu+ versus Her2/neu−, P=0.023), and 5-year survival (overall, P=0.05) of breast cancer patients. Next, the relationship between α9-nAChR expression levels and survival time after the surgical treatments was explored. Fifty-five patients were followed up for an average of 5.5 years after surgery (ranging from 5 to 6 years). 16 of the 55 patients (29%) had died of breast cancer. The 5-year disease-specific survival rate for the entire patient cohort was 71%. As shown in FIG. 1, there was a significant association between the clinical stage and outcome (through stage I-IV, overall P=0.009). Patients with stage IV breast cancer demonstrated the lowest 5-year survival rate (25%, dead/alive=3/1, total=4 patients, P=0.04) compared with patients with stage I breast cancer (100%). The overall 5-year survival rates of patients with stage II and III breast cancer were 81.25% (dead/alive=6/26, total=32 patients, P=0.365) and 62.5% (dead/alive=6/10, total=16 patients, P=0.23), respectively (FIG. 1, A).

As shown in Table 1, an increase in the expression of α9-nAChR mRNA in tumor versus normal tissue was detected in samples obtained from patients with advanced stages of breast cancer (mean fold ratios of 10.3 and 25.2 for stages III and IV, respectively), whereas α9-nAChR mRNA expression levels in tissue samples collected from patients with stage I breast cancer were only 3.1-fold higher than those detected in normal tissue (overall, *P=0.031). Next, it was evaluated the 5-year disease-specific survival rates according to the α9-nAChR expression levels (FIG. 1, B). The results revealed a significant association between the α9-nAChR expression levels (mean fold ratios of the tumor/normal pairs) in tumor tissue and the 5-year disease-specific survival rates (overall, P=0.009). High levels (i.e., mean fold ratios>10) of α9-nAChR expression in breast tumors were associated with the lowest 5-year disease-specific survival rate (50%, dead/alive=4/4, total=8 patients, P=0.006) compared to the low levels (i.e., expression levels less than one-fold higher than normal tissue) of α9-nAChR mRNA expression (88%, dead/alive=3/22, total=25 patients). Breast cancer patients that exhibited moderate increases in α9-nAChR expression levels (i.e., mean fold ratios>1 to ≤10) also presented a better survival rate (59%, dead/alive=9/13, total=22 patients, P=0.034) in comparison to those with low levels of α9-nAChR expression.

Example 2

Increased mRNA Expression Levels of α9-nAChR in ER+ Breast Tumor Tissue

Figure 2:
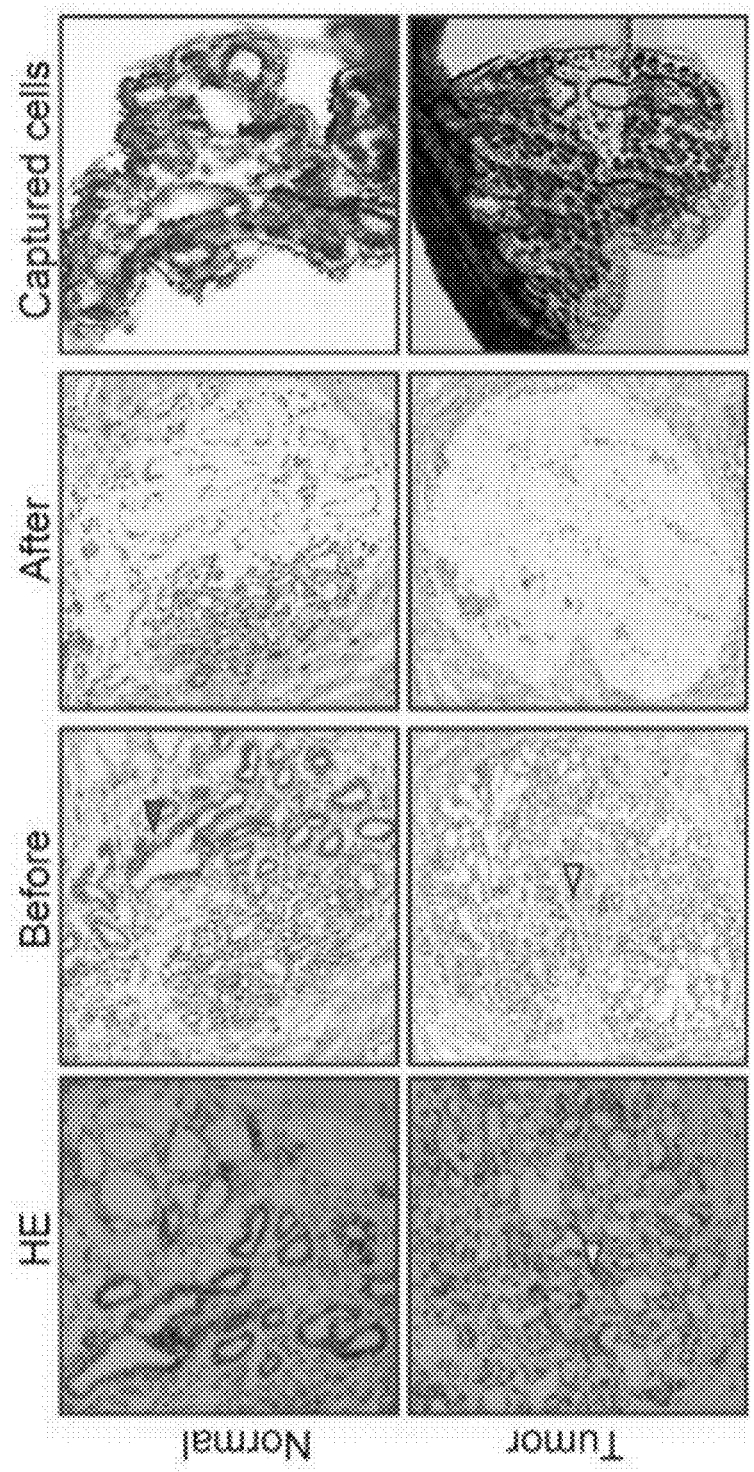
FIG. 2 shows α9-nAChR mRNA expression as determined by real-time PCR analysis. The population figures of at-risk patients in each group are listed in Table 1. A) LCM was performed for the ER+ and ER− breast tumor tissues. Left H.E.-stained tumor tissue sections from representative cases that possessed normal (upper) and tumor (lower) cells before microdis section. Scale bar=100 μm. Right Cells that were captured and transferred to the film on the LCM cap. Middle green and yellow arrowheads indicate normal and tumor cells, respectively. B) The mRNA expression levels of α9-nAChR in LCM captured cells were determined by real-time PCR analysis. The mRNA expression levels of α9-nAChR in the ER+ group were significantly different from those in the ER− group. The data were analyzed using the Student's t-test; all P-values are two-sided ($^\#$P=0.001). T tumor, N normal.
Figure 2:
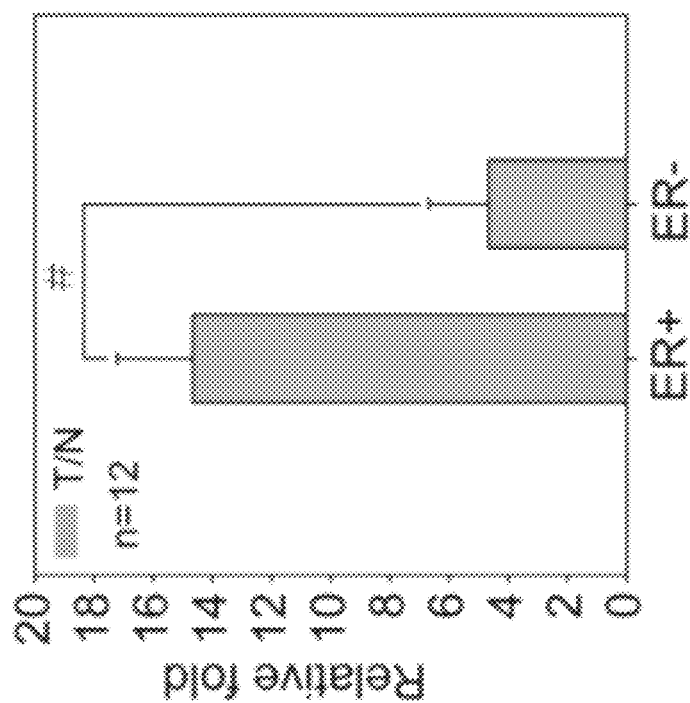

As shown in Table 1, whether the higher α9-nAChR mRNA expression levels detected in tumor tissues were associated with clinical diagnosis markers (i.e., ER, PR, and HER-2) was further tested. The α9-nAChR mRNA mean fold ratios detected in ER+ tumor tissues were higher than those detected in ER-tumors tissues (ER+ versus ER−; n=160 vs. 72; fold=11±3 vs. 6.7±2.3, *P=0.045). To further confirm these observations, microdissected tumor and normal cell clusters were individually harvested by LCM from 12 different tumor samples (FIG. 2, A and B, ER+ versus ER−, n=6 per group). In agreement with the initial findings, an increase in the expression of α9-nAChR was preferentially detected in LCM-dissected ER+ tumor cells in comparison to ER-tumor cells (FIG. 2, B, bars 1 versus 2, #P=0.001).

Example 3

Effects of Nicotine and E2 on Breast Cancer Cell Growth

Figure 3:
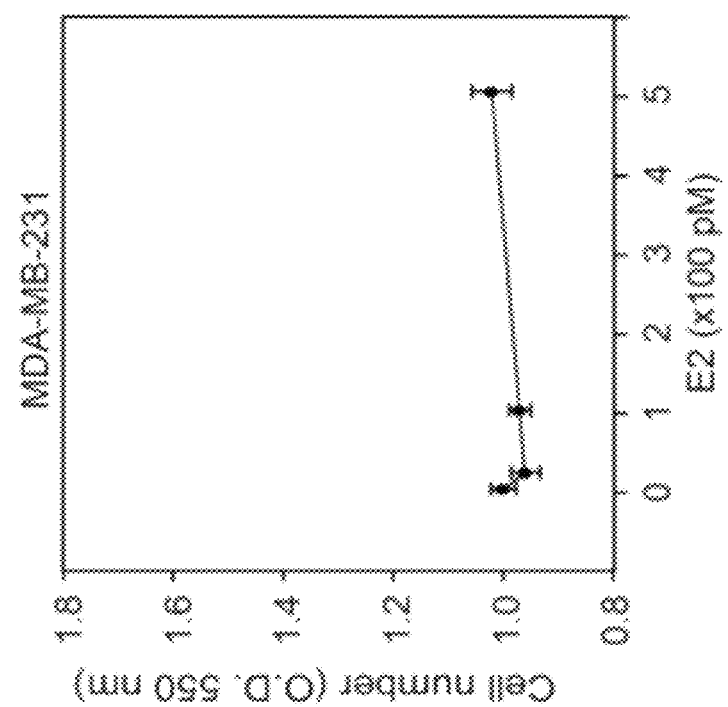
FIG. 3 shows effects of nicotine and E2 on the growth of human breast cancer cells. A), C) MCF-7 and B), D) MDA- MB-231 cells were cultured as described in "Materials and methods" and incubated with different concentrations of nicotine or E2 for 24 h. The cells were then counted using the MTT assay at an OD of 550 nM. All of the MTT assays were performed in triplicate.
Figure 3:
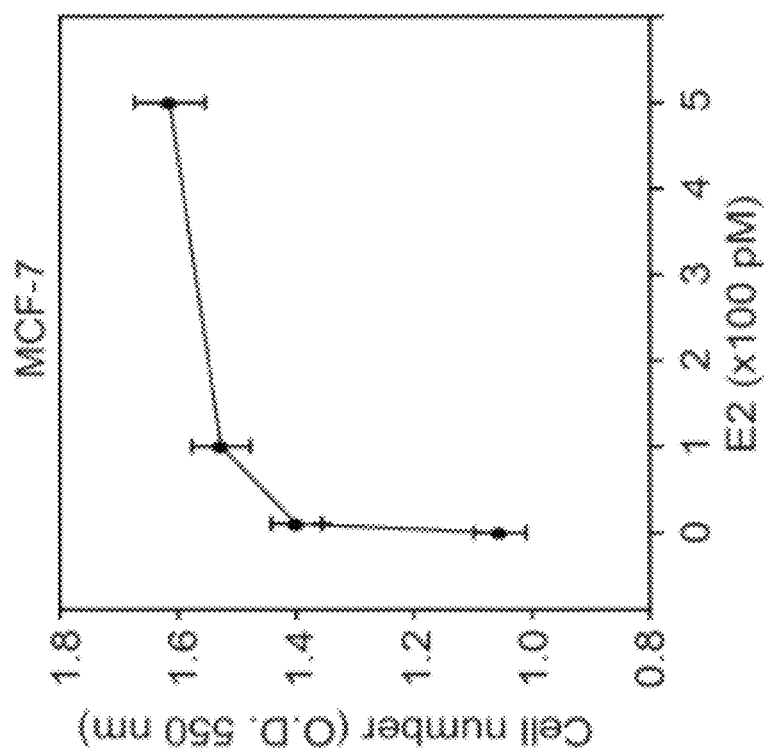
Figure 3:
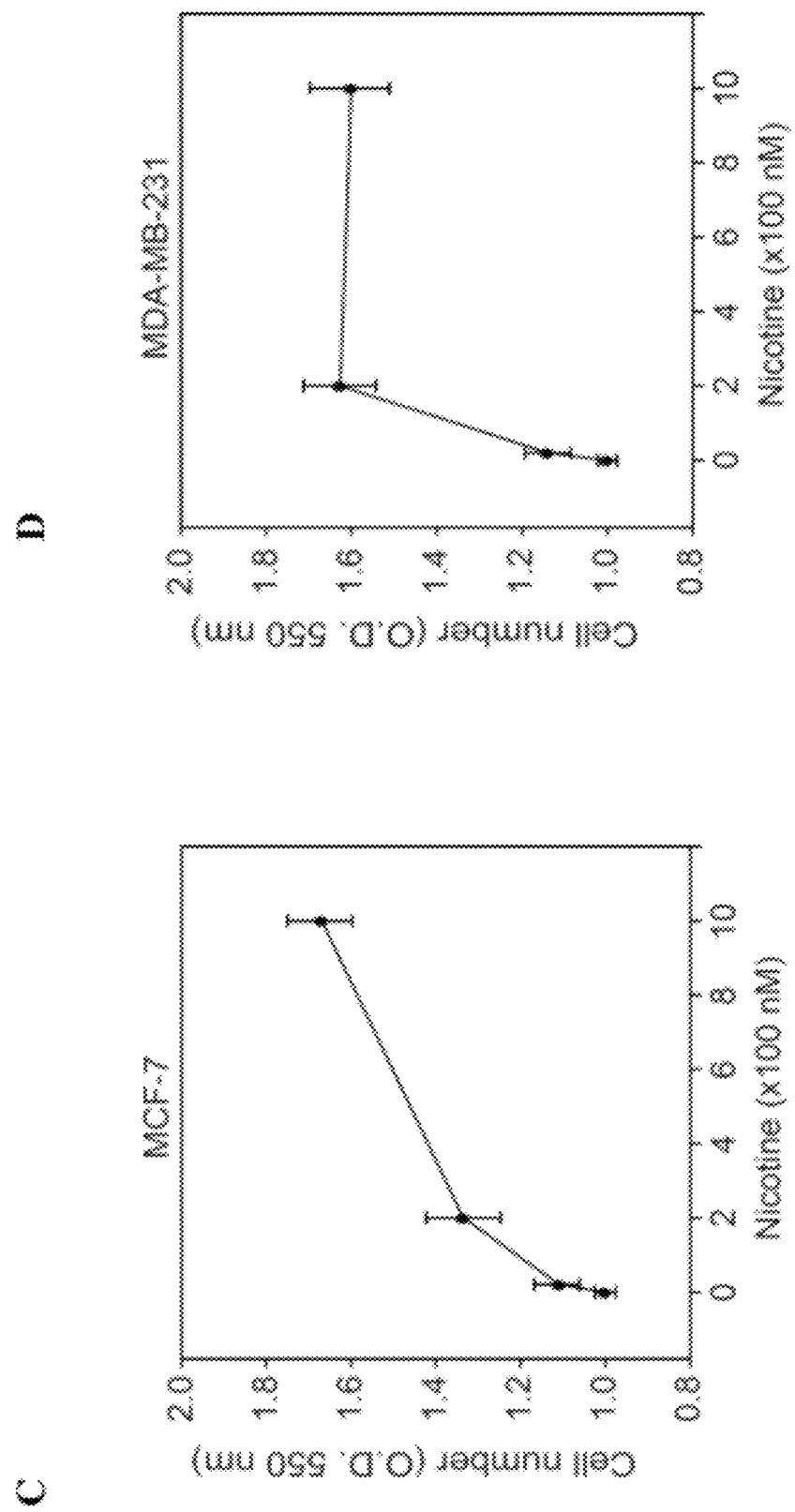

To determine whether the signaling of nicotine or E2 via activation of their cognate receptors (α9-nAChR and ERα, respectively) was involved in cancer cell proliferation, cell growth proliferation assays were performed using breast cancer cells with or without ER expression (FIG. 2). The results showed a significant increase in cell proliferation in E2 (>100 pM) treated MCF-7 (ER+/α9-nAChR+) cells when compared to MDA-MB-231 (ER−/α9-nAChR+) cells (FIGS. 3A and B). To test whether nicotine treatment affected the proliferation of these cell lines, cell growth curves were generated. The nicotine-induced cell growth curves were similar for both cell lines (FIG. 3, C and D).

Example 4

Figure 4:
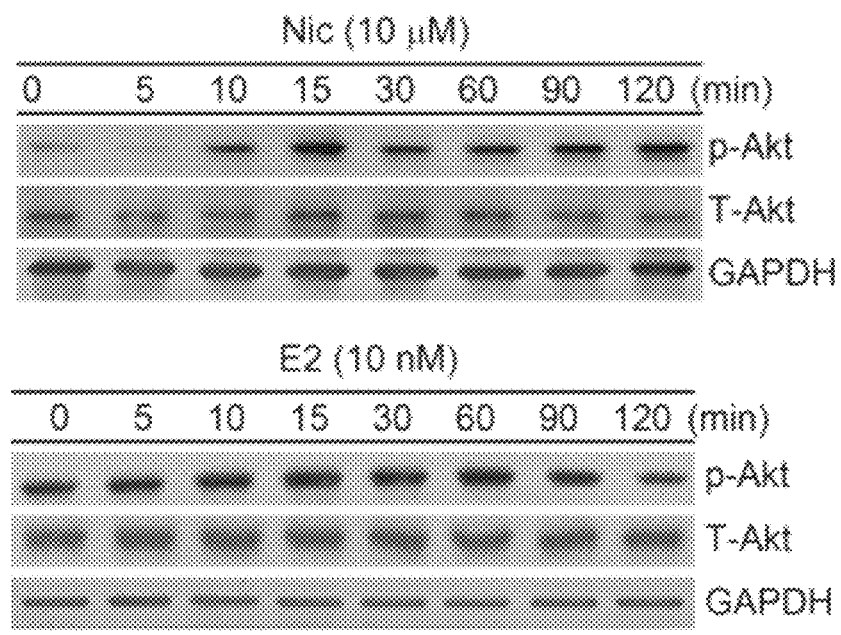
FIG. 4 shows nicotine and E2-induced up-regulation of p-Akt in MCF-7 cells. MCF-7 cells were treated with either nicotine or E2 in A) time and B) dose-dependent manner. Both p-AKT and total (T)-AKT protein expression were detected by immunoblotting analysis. The membrane was then re-probed with a GAPDH antibody to ensure equal protein loading.
Figure 4:
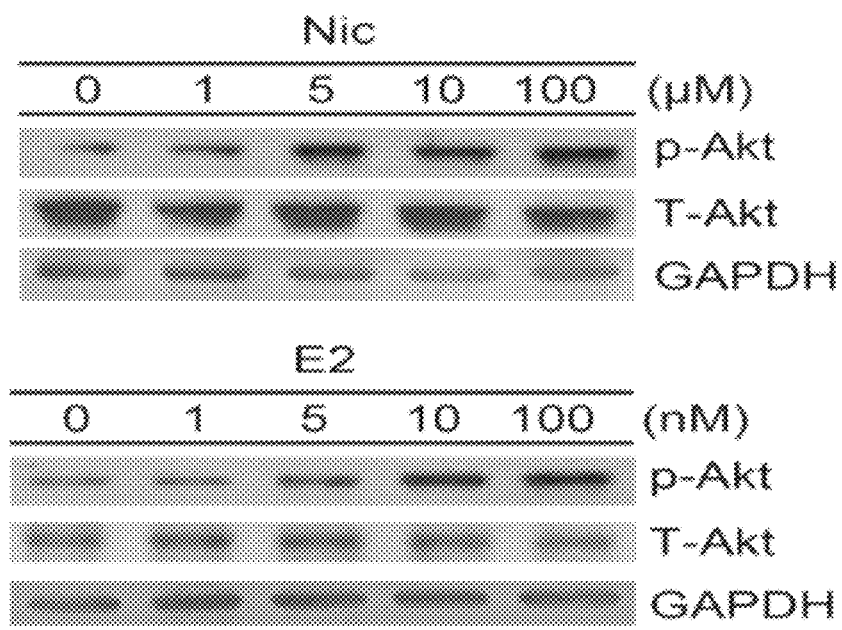
Figure 5:
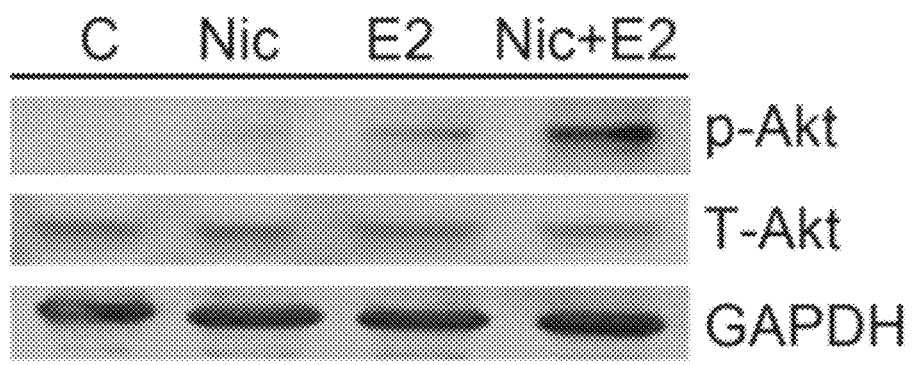
FIG. 5 shows combined treatment of nicotine and E2 in the up-regulation of p-Akt in MCF-7 cells. MCF-7 cells were treated with nicotine (5 μM), E2 (5 nM) or a combination of both agents for 15 min. Both p-AKT and T-AKT protein expression were detected by immunoblotting analysis. The membrane was then re-probed with a GAPDH antibody to ensure equal protein loading.

Nicotine- and E2-Induced Cell Proliferation Occurs Through Activation of the Akt Signaling Pathway in MCF-7 Cells Akt is activated via phosphorylation of either its serine (Ser$^{473}$) or threonine (Thr$^{308}$) residues by various upstream stimulatory factors. To determine whether Akt activation is involved in nicotine-induced cell proliferation, MCF-7 cells were treated with nicotine (10 μM) in a time-dependent manner for immunoblotting analysis. The results demonstrated that nicotine application significantly increased p-Akt (Ser$^{473}$) expression in MCF-7 cells within 10 min of the treatment and caused a persistent increase in p-Akt (Ser$^{473}$) expression for the duration of the experiment (FIG. 4, A, lanes 3-8). Similarly, increased p-Akt (Ser$^{473}$) protein levels were also detected in MCF-7 cells after 15 min of treatment with 10 nM E2 (FIG. 4, A, lane 4). However, the E2induced increase in p-Akt (Ser$^{473}$) expression was down-regulated 120 min later (FIG. 4, A, lane 8). Subsequently, an experiment to examine the dose-dependent effects of nicotine and E2 on p-Akt (Ser$^{473}$) protein expression levels in MCF-7 cells was performed. The results showed that the minimum concentrations of nicotine and E2 required for p-Akt (Ser$^{473}$) induction within 15 min were 5 μM and 5 nM, respectively (FIG. 4, B, lane 3). Next, the combined effects of nicotine and E2 on Akt activation in MCF-7 cells were examined. MCF-7 cells were treated with either nicotine (5 μM) alone, E2 (5 nM) alone, or both reagents for 15 min, and p-Akt(Ser$^{473}$) was then detected by immunoblotting analysis. It was found that the combined treatment with nicotine enhanced E2-induced Akt (Ser$^{473}$) phosphorylation (FIG. 5, lane 4).

Example 5

Nicotine and E2 Activate MAP Kinase, Which Phosphorylates ERα in MCF-7 Cells

Previous studies have demonstrated that the up-regulation of PI3K/Akt signaling by E2 occurs through the activation of ERα but not ERβ(37). In response to E2 binding, Ser$^{104/106}$ and Ser$^{118}$ are the primary ERα sites that are phosphorylated by the ERK1/2 MAP kinase. However, ERα (Ser$^{167}$) is the primary site of phosphorylation via the PI3-kinase/Akt pathway (Pasapera Limon, A. M., Herrera-Munoz, J., Gutierrez-Sagal, R., and Ulloa-Aguirre, A. 2003. *The phosphatidylinositol 3-kinase inhibitor LY294002 binds the estrogen receptor and inhibits 17beta-estradiol-induced transcrip-*

*tional activity of an estrogen sensitive reporter gene. Mol Cell Endocrinol* 200:199-202). A recent study has suggested that ERα phosphorylation at these different phosphorylation sites can affect the survival of ER-positive breast cancer patients who are undergoing endocrine therapy (Yamashita, H., Nishio, M., Toyama, T., Sugiura, H., Kondo, N., Kobayashi, S., Fujii, Y., and Iwase, H. 2008. *Low phosphorylation of estrogen receptor alpha (ERalpha) serine* 118 *and high phosphorylation of ERalpha serine* 167 *improve survival in ER-positive breast cancer. Endocr Relat Cancer* 15:755-763). Accordingly, the induction of ERα phosphorylation at different sites by carcinogenic factors (such as hormones and smoking) may play an important role in breast cancer formation.

Figure 6:
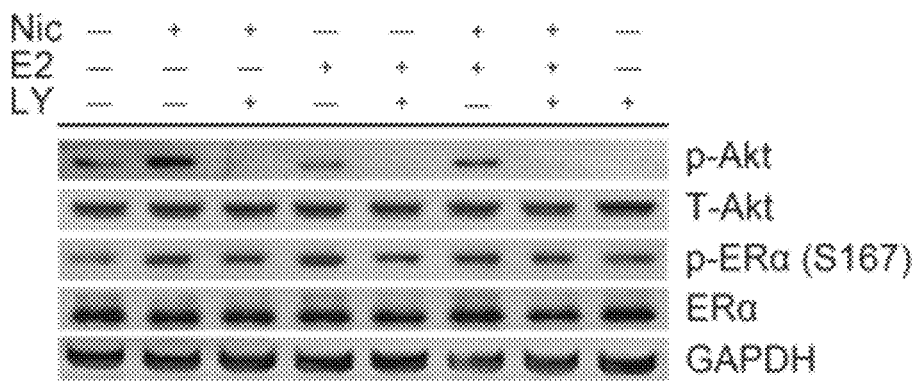
FIG. 6 shows Akt and MAPK signaling kinases mediate ERα phosphorylation induced by nicotine and E2 in MCF-7 cells. MCF-7 cells were pretreated for 30 min with or without inhibitors specific for Akt and MAPK kinases, including A) PI3K (LY294002, 10 μM), B) ERK1/2 (PD98059, 25 μM), and C) JNK (SP600125, 25 μM), and then with nicotine (10 μM) or E2 (10 nM) for an additional 30 min. After treatment, the cells were harvested for immunoblotting analysis. The p-ERα, total ER-α, and MAPK kinase proteins levels were detected by immunoblotting analysis.
Figure 6:
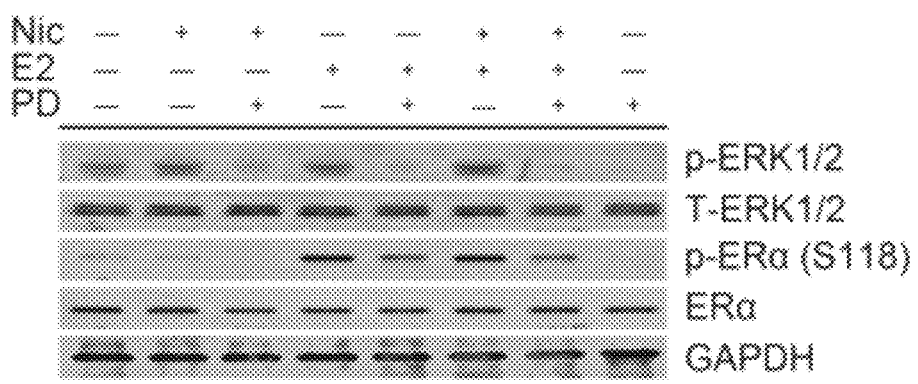
Figure 6:
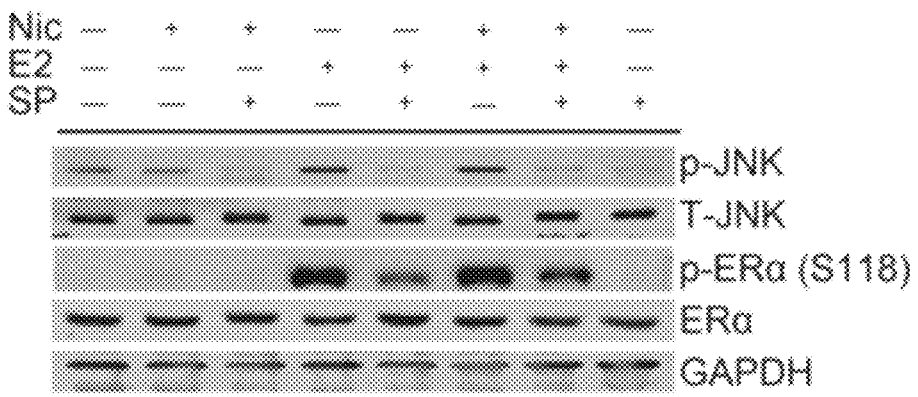
Figure 7:
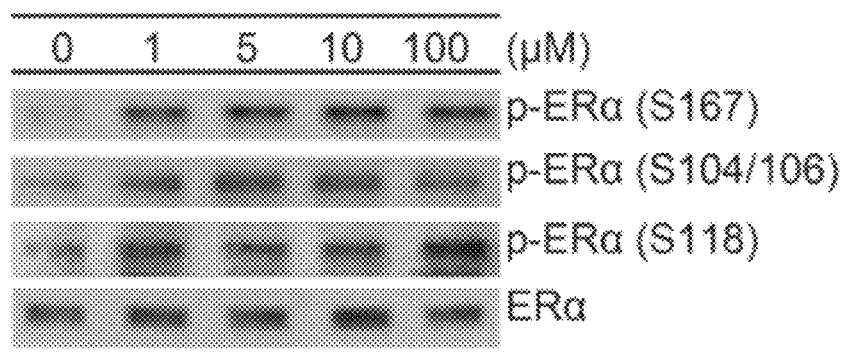
FIG. 7 shows nicotine and E2 induced ERα phosphorylation in MCF-7 cells. MCF-7 cells were treated with A) nicotine (1-100 μM) or B) E2 (1-100 nM) for 30 min and then harvested for immunoblotting analysis. p-ER-α and total ER-α protein levels were then detected.
Figure 7:
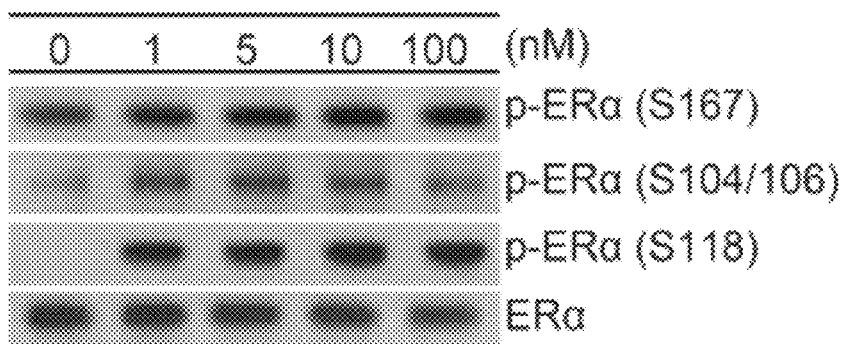

To test the above, MCF-7 cells were pretreated with the PI3K inhibitor Ly294002 (10 μM) for 30 min before an additional 30-min incubation in the presence or absence of either E2 (10 nM) or nicotine (10 μM). The results revealed that the pretreatment of cells with Ly294002 almost completely abolished the nicotine-induced increase in p-Akt (Ser$^{473}$) protein levels (FIG. 6, A, lanes 3). However, the nicotine-induced ERα (Ser$^{167}$) phosphorylation was inhibited to a lesser degree (FIG. 6, A, lanes 3). These results suggested that nicotine-induced ERα (Ser$^{167}$) phosphorylation was only partially induced via the PI3K/Akt signaling pathway. Furthermore, it was demonstrated that ERK1/2 and JNK kinases were also activated by E2 treatment in breast cancer cells (FIG. 6, B and C, lanes 4). Pretreatment of the cells with the specific MAPK inhibitors PD98059 and SP600125 almost completely abolished the E2-induced increase in p-ERK1/2 and p-JNK protein levels, respectively (FIG. 6, B and C, lanes 5). These results indicated that the E2-induced activation of ERK1/2 and JNK kinases was also involved in ERα (Ser$^{118}$) phosphorylation. To determine the minimum concentration of nicotine and E2 required for affecting the specific sites of ERα phosphorylation in MCF-7 cells, an immunoblotting analysis was performed. As shown in FIG. 7, A and B, ERα phosphorylation at Ser residues was easily detected in MCF-7 cells treated with concentrations of nicotine as low as 1 μM or concentrations of E2 as low as 1 nM at 30 min after drug treatment.

Example 6

Nicotine- and E2-Induced ER Activates α9-nAChR Gene Transcription

Figure 8:
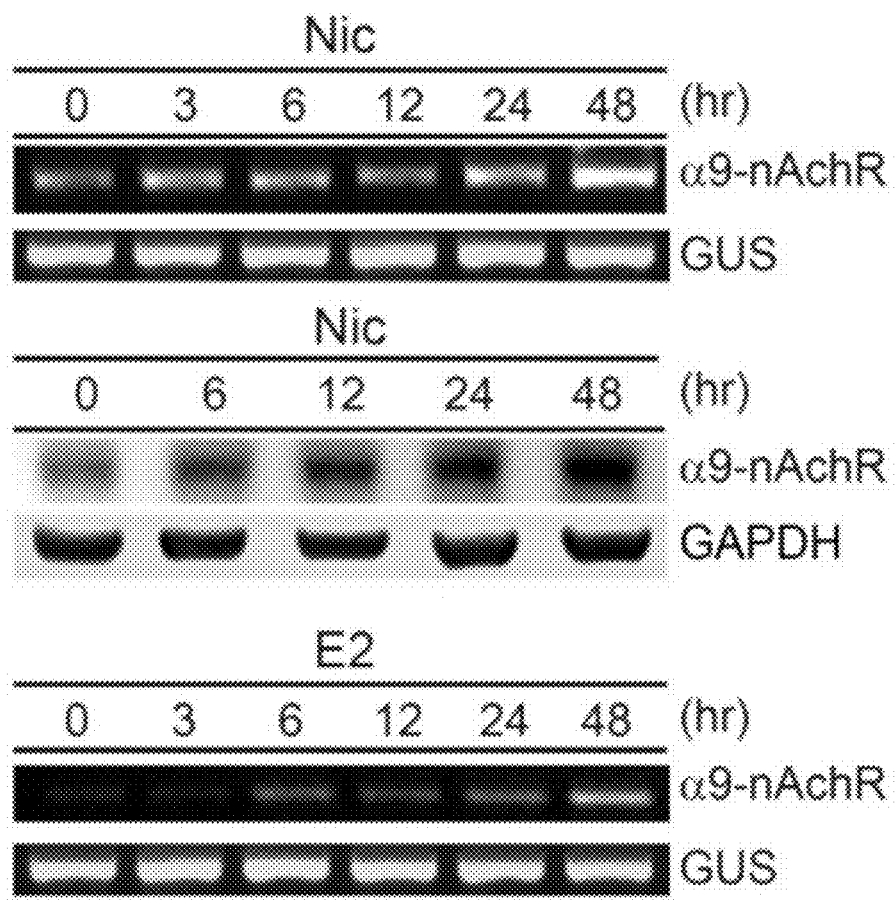
FIG. 8 shows nicotine and E2 induced α9-nAChR transcriptional regulation in MCF-7 cells. MCF-7 cells were treated with nicotine (10 μM) or E2 (10 nM) in a time-dependent manner. After treatment, the cells were harvested, and α9-nAChR mRNA and protein expression levels were determined by RT-PCR and immunoblotting analyses.
Figure 9:
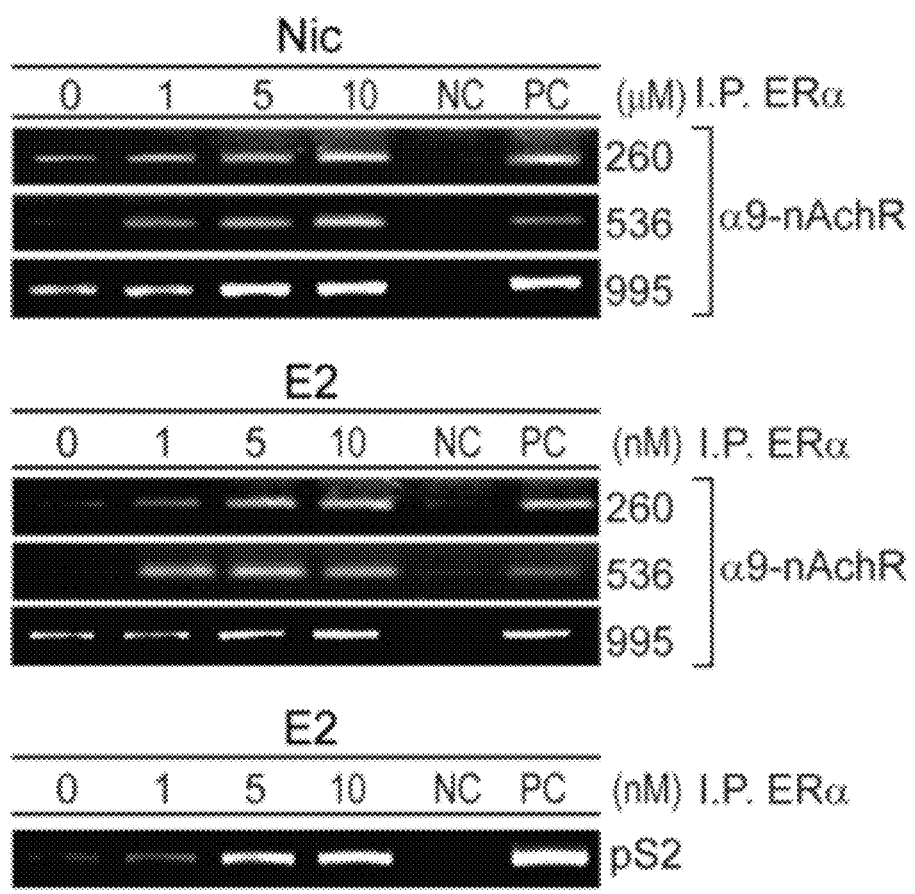
FIG. 9 shows ERs confer α9-nAChR transcriptional regulation by nicotine and E2 in MCF-7 cells. MCF-7 cells were treated with nicotine or E2 for 6 h. After treatment, the cell lysates were harvested, and ER-bound DNA was precipitated using an ER-specific antibody for ChIP. PCR analysis was performed using three independent primer pairs targeting different regions of the α9-nAChR promoters; they were designed to amplify the regions from −260, −536 and −995 to −1. To determine whether the E2-induced recruitment of ERs was functionally sufficient to activate down-stream gene promoters (such as PS2), ChIP was performed using MCF-7 cells. The data are representative of three independent experiments that provided similar results. Genomic DNA isolated from MCF-7 cells was used as a positive input control (PC) to evaluate the PCR conditions. NC negative control.

As described above, higher α9-nAChR mRNA expression levels were preferentially detected in ER+ breast tumor tissues (Table 1; FIG. 2, B). To investigate whether α9-nAChR gene expression is transcriptionally regulated by the ER, α9nAChR mRNA/protein levels were detected in MCF-7 cells that were exposed to nicotine or E2 in a time-dependent manner. The results revealed that α9-nAChR mRNA and protein expression levels were significantly induced at 6 h post-treatment with nicotine (10 μM) or E2 (10 nM) (FIG. 8). To further demonstrate that the ER is a transcription factor that directly binds to the α9-nAChR promoter in response to E2 and nicotine treatment, ChIP assays were performed using MCF-7 cells that had been treated with either E2 or nicotine. Our results demonstrated that the ER was directly bound to the α9-nAChR promoter region at three different locations (−260, −536 and −995 to −1) after treatment with nicotine (>5 μM) or E2 (>5 nM) for 6 h (FIG. 9). To test whether the E2-induced ER recruitment was functionally involved in downstream gene promoter activation, ChIP was performed using MCF-7 cells. The results showed that both α9-nAChR and PS2 could be transcriptionally up-regulated by the ER through the direct binding of the receptor to its promoter target in response to E2 treatment (FIG. 9). ERs can also act indirectly by altering the activities of other transcription factors (e.g., Sp1, AP1, or NF-κB) at their cognate sites on DNA. FIG. 5c shows the potential transcription factor response elements in the promoter regions of α9-nAChR, including two AP1 sites and one vitamin D receptor (VDR) site, which are responsive to ER binding.

Figure 10:
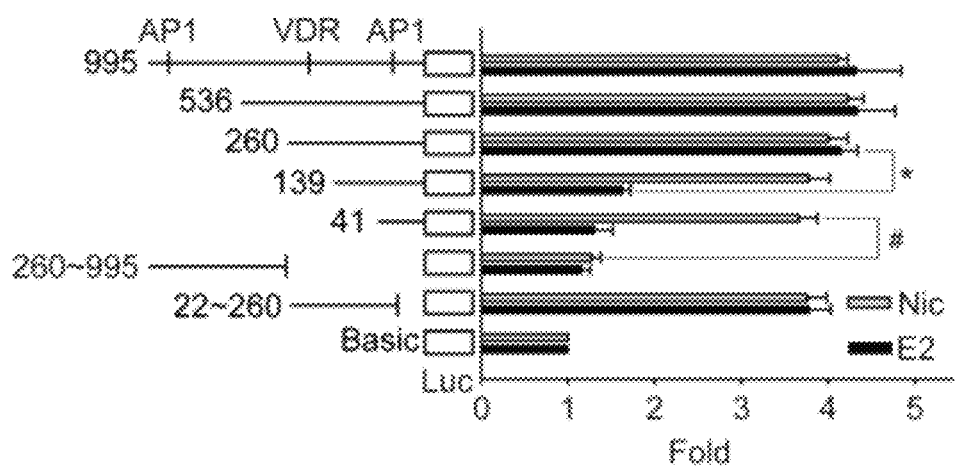
FIG. 10 shows regulation of the α9-nAChR promoter region by nicotine or E2. A) Schematic representation of the α9-nAChR promoter region (−996/−1) illustrating the putative AP1 and VDR transcription factor-binding sites. Right panel MCF-7 cells were transiently transfected with pGL3 (α9-nAChR) and pRL-TK plasmids for 24 h before treatment with nicotine (10 μM) or E2 (10 nM) for an additional 24 h. Cell lysates were harvested, and relative firefly luciferase activities were measured and normalized to renilla luciferase activities in the same cell lysates. The luciferase activity in the cells transfected with vehicle plasmid (0.1% DMSO for E2 and ddH2O for nicotine) were defined as a onefold change. B) MCF-7 cells were transiently transfected with either pGL3 (AP1)5 or pGL3(mAP1)5 plasmid for 24 h and then treated with nicotine (0.1-10 μM) for an additional 6 h. The luciferase activity was assayed and normalized to the pRL-TK expression as described above. Cells treated with nicotine were compared to vehicle-treated controls (*P=0.009). The data were analyzed using nonparametric tests; all P-values are two-sided.
Figure 10:
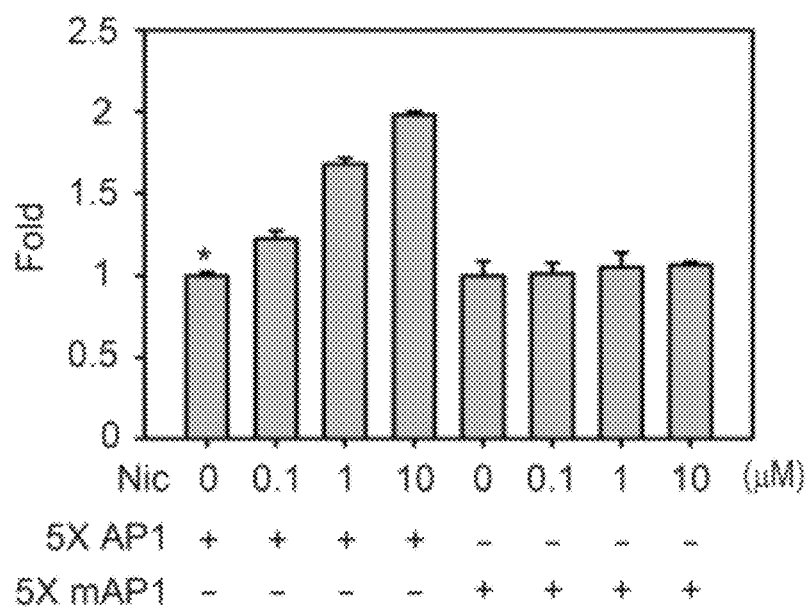

To more precisely define the regulatory elements that are required by the α9-nAChR promoter for ER-induced transcriptional activation, transient-transfection experiments were conducted using a series of 5' promoter deletion constructs in pGL3 vectors that were transfected into MCF-7 cells. Specific response elements in the α9-nAChR promoter were eliminated in the shorter constructs (FIG. 10, A). In these experiments, the luciferase activity observed in the cells that were transfected with the empty vector was defined as a one-fold change (i.e., basal level). Experiments using the full-length construct demonstrated that the α9-nAChR promoter activity was significantly induced (greater than four-fold) by E2 (10 nM) or nicotine (10 μM) treatment after 24 h in MCF-7 cells (FIG. 10, A, *P<0.05). In addition, the E2- and nicotine-induced responsiveness was preserved when a region of the promoter spanning positions −995 to −260 was deleted (FIG. 10, A). In contrast, E2-induced luciferase activity was abolished when a region of the α9-nAChR promoter spanning positions −260 to −139 was deleted (*P=0.01). These results suggested that the E2-induced ER-responsive element was located at the VDR site (−181 to −167, sequence, aggggaggGAGGgca, SEQ ID NO:12). It was further demonstrated that nicotine-induced luciferase activity was abolished when a region of the α9-nAChR promoter spanning positions −41 to −1 was deleted (#P=0.01), and the nicotine-induced ER-responsive element was suggested to be located at the AP1 site (−37 to −27, sequence, ccTGACtgaga, SEQ ID NO:5). Whether the AP1 DNA-binding sites that appeared in the α9-nAChR promoter were important for nicotine stimulation in MCF-7 cells was next determined. To explore this matter, cells were transfected with pGL3(AP1)5, a luciferase reporter plasmid, which contains five repetitive AP1 DNA-binding sites from the α9-nAChR gene promoter (−37 and −27). The results demonstrated that nicotine increased the AP1-linked luciferase activity in a dose-dependent manner (FIG. 10, B, lanes 2-4). Mutated AP1 DNA-binding sequences were cloned into the luciferase reporter construct pGL3(mAP1)5 and transfected into MCF-7 cells as negative controls for the nicotine treatment (FIG. 10, B, lanes 5-8).

Example 7

Figure 11:
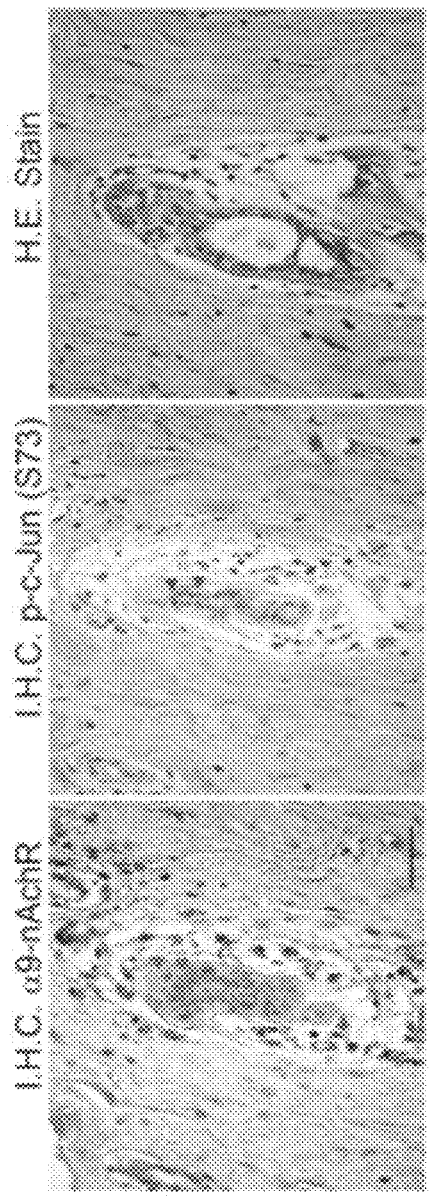
FIG. 11 shows ER and AP1 confer α9-nAChR transcriptional regulation in human breast cancer tissues. A) Activated AP1 (p-c-Jun, Ser73) and α9-nAChR were detected in the same regions of human invasive ductal and lobular carcinoma breast tumor tissues. Serial tumor tissue sections (5-7-μM thick) were stained with specific antibodies against human α9-nAChR (left, green arrowhead) and activated AP1 (p-c-Jun, Ser73) (middle, red arrowhead). The sections were stained with H.E. Scale bar=200 μm. B) ER+ or ER− human breast cancer patients were randomly selected (n=2 per group). Tumor and normal tissue lysates were harvested, and AP1-bound DNA complexes were precipitated using an activated AP1 (p-c-Jun, Ser73)-specific antibody for ChIP. The RT-PCR data (upper) are representative of three independent experiments that provided similar results. The samples used for ChIP were also assayed by real-time PCR (lower) to obtain a quantitative analysis. Genomic DNA isolated from MCF-7 cells was used as a positive input control (PC) to evaluate the PCR conditions. NC negative control; N, T normal and tumor tissues, respectively.
Figure 11:
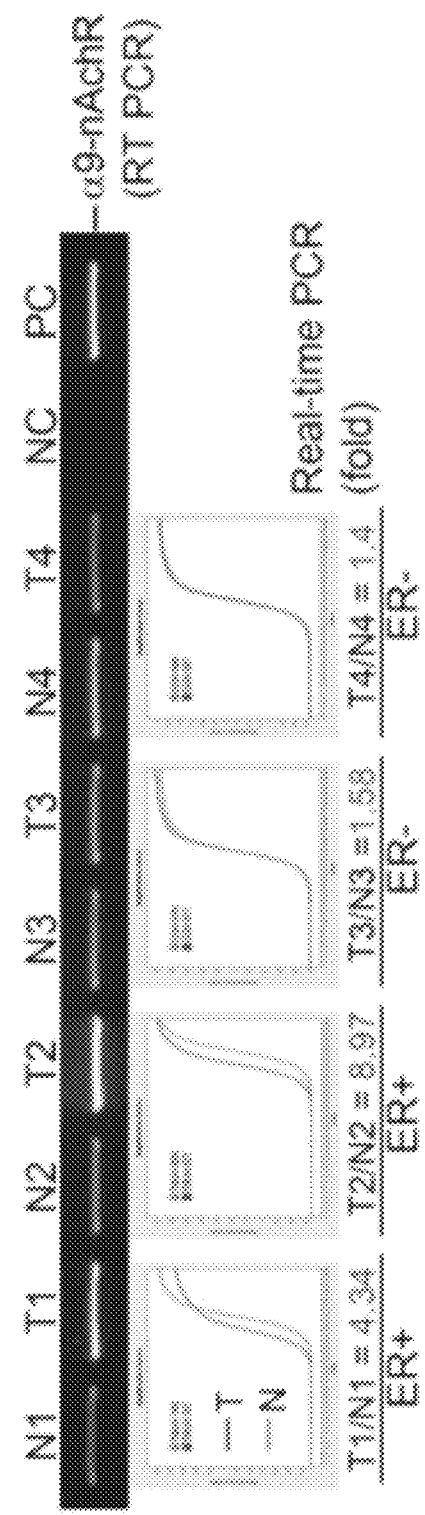
Figure 12:
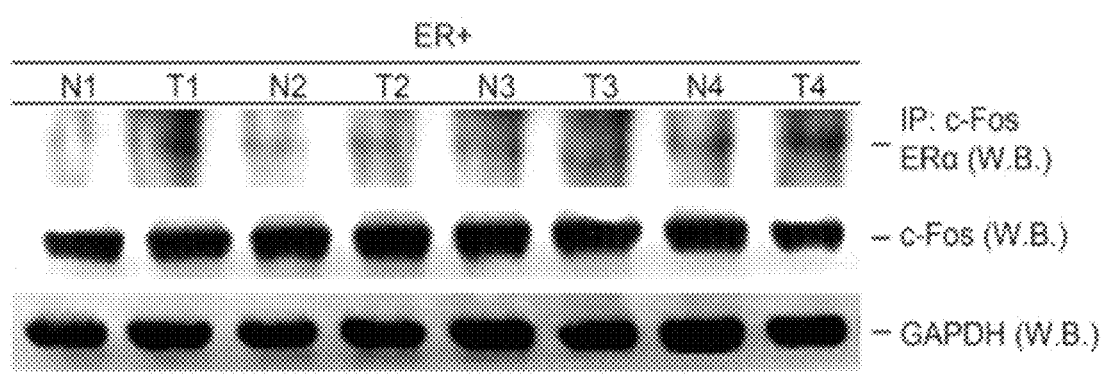
FIG. 12 shows direct interaction of ER and AP1 in four breast tumor tissue pairs. ER+ human breast cancer patients were randomly selected (n=4). The tumor and normal tissues were dissected separately, and protein was harvested for immunoprecipitation using an AP1 (c-Fos)-specific antibody. Subsequently, the protein level of ER was assessed by immunoblotting analysis. The expression levels of both total c-Fos and GAPDH were detected by immunoblotting as protein loading controls.

Effect of AP1 Activation on the Over-Expression of α9-nAchR in Breast Cancer Tissues To test whether the over-expression of α9-nAchR in human breast tumor tissue was regulated by AP1, an immunohistochemical staining analysis was performed. As shown in FIG. 11, A, positively stained cells (indicated by brown color) were simultaneously detected in serial sections of breast tumor tissue and revealed α9-nAchR protein expression in the cytosol (indicated by the green arrowhead). In contrast, active AP1 (c-Jun-p, Ser$^{73}$) was found in the nuclear region (indicated by the red arrowhead). To test whether AP1 plays an important role in the transcriptional regulation of α9-nAchR protein expression, ChIP analysis was performed using samples from breast tumor patients with different ER statuses (n=2 per group). Tumor and normal tissue lysates were harvested, and AP1-bound DNA complexes were precipitated using an activated AP1 (p-c-Jun, Ser[73])-specific antibody for ChIP. The results demonstrated significant AP1 binding to the α9-nAchR promoter in ER+ tumor tissues in comparison to normal tissue (FIG. 11, B, upper lanes 2 and 4 versus 1 and 3). In contrast, the levels of AP1 binding to the α9-nAchR promoter were less profound in ER-tumor tissues (FIG. 11, B, upper, lanes 6 and 8 versus 5 and 7). The samples used for the ChIP assay was also analyzed by real-time PCR (lower panel) to quantify the fold changes in AP1/α9-nAchR promoter-binding activity in ER+ tumor tissues in comparison to ER-tumor tissues, and a change of more than a four- to eightfold was detected (FIG. 11, B, lower panel). To ascertain whether the ERs were affected by direct binding to their relevant ER-binding sites located in the α9-nAchR promoter (such as the VDR site spanning positions −181 to −167) or whether the binding was indirectly associated with AP1 followed by binding to the α9-nAchR promoter (such as the AP1 site spanning positions −36 to −26), immunoprecipitation was performed using an AP1 (c-Fos)-specific antibody followed by detection of the ER protein levels by immunoblotting analysis (FIG. 12). Four randomized ER+ patients were selected, and an increased level of ER/AP1 complex formation was detected in tumor tissues in comparison to normal tissues (FIG. 12, lanes 2, 4, 6, and 8 versus 1, 3, 5, and 7, respectively). The c-Fos and GAPDH protein levels were detected by immunoblotting analysis to ensure equal levels of protein loading.

What is claimed is:

1. A method of identifying a candidate compound which may inhibit overexpression of α9-nAChR in nicotine-derived-compound-induced breast cancer cells in an advanced stage, comprising contacting the compound with the AP1 polypeptide or VDR polypeptide and determining whether the compound binds to the polypeptide, wherein binding of the compound to the polypeptide indicates that the compound may inhibit overexpression of α9-nAChR in nicotine-derived-compound-induced breast cancer cells in an advanced stage; wherein the AP1 polypeptide is encoded by a polynucleotide comprising a sequence of nnTGAC(or G)nnnnn (SEQ ID NO:1 or SEQ ID NO:2), and wherein the VDR polypeptide is encoded by a polynucleotide comprising a sequence of nnnnnnnnGAGG(or T)nnn (SEQ ID NO:3 or SEQ ID NO:4).

2. The method of claim 1, wherein the AP1 polypeptide is encoded by a polynucleotide comprising a sequence of ccTGACtgaga (SEQ ID NO:5), and wherein the VDR polypeptide is encoded by a polynucleotide comprising a sequence of aggggaggGAGGgca (SEQ ID NO:12).

3. A method of identifying a candidate compound which may inhibit overexpression of α9-nAChR in nicotine-derived-compound-induced breast cancer cells in an advanced stage, comprising contacting the AP1 polypeptide or VDR polypeptide and an estrogen receptor polypeptide with the compound and determining the ability of the compound to interfere with the binding of the estrogen receptor polypeptide with the AP1 polypeptide, wherein interference of the binding of the estrogen receptor polypeptide and the AP1 polypeptide indicates the compound may inhibit overexpression of α9-nAChR in nicotine-derived-compound-induced breast cancer cells; wherein the AP1 polypeptide is encoded by a polynucleotide comprising a sequence of nnTGAC(or G)nnnnn (SEQ ID NO:1 or SEQ ID NO:2) and wherein the VDR polypeptide is encoded by a polynucleotide comprising a sequence of nnnnnnnnGAGG(orT)nnn (SEQ ID NO:3 or SEQ ID NO:4).

4. The method of claim 3, wherein the AP1 polypeptide is encoded by a polynucleotide comprising a sequence of ccTGACtgaga (SEQ ID NO:5) and wherein the VDR polypeptide is encoded by a polynucleotide comprising a sequence of aggggaggGAGGgca (SEQ ID NO:12).

* * * * *

```
                            SEQUENCE LISTING

<160> NUMBER OF SEQ ID NOS: 33

<210> SEQ ID NO 1
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: n is a, t, c or g

<400> SEQUENCE: 1
nntgacnnnn n                                                         11

<210> SEQ ID NO 2
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: n is a, t, c or g

<400> SEQUENCE: 2
nntgagnnnn n                                                         11

<210> SEQ ID NO 3
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: n is a, t, c or g

<400> SEQUENCE: 3
nnnnnnnnga ggnnn                                                     15

<210> SEQ ID NO 4
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: n is a, t, c or g

<400> SEQUENCE: 4
nnnnnnnnga gtnnn                                                     15

<210> SEQ ID NO 5
<211> LENGTH: 11
```

```
<212> TYPE: DNA
<213> ORGANISM: Homo sapiens
<220> FEATURE:
<221> NAME/KEY: misc_feature
<222> LOCATION: (1)..(11)

<400> SEQUENCE: 5
cctgactgag a                                                          11

<210> SEQ ID NO 6
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: n is a, t, c or g

<400> SEQUENCE: 6
natgagtcag n                                                          11

<210> SEQ ID NO 7
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: n is a, t, c or g

<400> SEQUENCE: 7
nttgagtcag n                                                          11

<210> SEQ ID NO 8
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: n is a, t, c or g

<400> SEQUENCE: 8
ngtgagtcag n                                                          11

<210> SEQ ID NO 9
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: n is a, t, c or g

<400> SEQUENCE: 9
natgagtcac n                                                          11

<210> SEQ ID NO 10
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: n is a, t, c or g

<400> SEQUENCE: 10
natgagtcag n                                                          11
```

```
<210> SEQ ID NO 11
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: n is a, t, c or g

<400> SEQUENCE: 11
natgagtcaa n                                                          11

<210> SEQ ID NO 12
<211> LENGTH: 15
<212> TYPE: DNA
<213> ORGANISM: Homo sapiens
<220> FEATURE:
<221> NAME/KEY: misc_feature
<222> LOCATION: (1)..(15)

<400> SEQUENCE: 12
aggggaggga gggca                                                      15

<210> SEQ ID NO 13
<211> LENGTH: 15
<212> TYPE: DNA
<213> ORGANISM: Homo sapiens
<220> FEATURE:
<221> NAME/KEY: misc_feature
<222> LOCATION: (1)..(15)

<400> SEQUENCE: 13
aggggaggga ggtca                                                      15

<210> SEQ ID NO 14
<211> LENGTH: 15
<212> TYPE: DNA
<213> ORGANISM: Homo sapiens
<220> FEATURE:
<221> NAME/KEY: misc_feature
<222> LOCATION: (1)..(15)

<400> SEQUENCE: 14
agggtcaaga ggtca                                                      15

<210> SEQ ID NO 15
<211> LENGTH: 15
<212> TYPE: DNA
<213> ORGANISM: Homo sapiens
<220> FEATURE:
<221> NAME/KEY: misc_feature
<222> LOCATION: (1)..(15)

<400> SEQUENCE: 15
gggtggaaga ggtca                                                      15

<210> SEQ ID NO 16
<211> LENGTH: 15
<212> TYPE: DNA
<213> ORGANISM: Homo sapiens
<220> FEATURE:
<221> NAME/KEY: misc_feature
<222> LOCATION: (1)..(15)

<400> SEQUENCE: 16
aaggtcaaga gttca                                                      15
```

```
<210> SEQ ID NO 17
<211> LENGTH: 15
<212> TYPE: DNA
<213> ORGANISM: Homo sapiens
<220> FEATURE:
<221> NAME/KEY: misc_feature
<222> LOCATION: (1)..(15)

<400> SEQUENCE: 17
gggtggaaga gtgtg                                                    15

<210> SEQ ID NO 18
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(18)

<400> SEQUENCE: 18
gtccagggtc ttgtttgt                                                 18

<210> SEQ ID NO 19
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(18)

<400> SEQUENCE: 19
atccgctctt gctatgat                                                 18

<210> SEQ ID NO 20
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(23)

<400> SEQUENCE: 20
agtgttccct gctagaatag atg                                           23

<210> SEQ ID NO 21
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 21
aaacagcccg tttacttgag                                               20

<210> SEQ ID NO 22
<211> LENGTH: 20
<212> TYPE: DNA
<213> ORGANISM: Artificial Sequence
```

```
<220> FEATURE:
<223> OTHER INFORMATION: primer
<220> FEATURE:
<221> NAME/KEY: misc_feature
<222> LOCATION: (1)..(20)

<400> SEQUENCE: 22
ctgatttggt cagcctttga                                               20

<210> SEQ ID NO 23
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(19)

<400> SEQUENCE: 23 cttttcctg agcctctat                                                 19

<210> SEQ ID NO 24
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 24
ctgatttggt cagcctttga                                               20

<210> SEQ ID NO 25
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 25
ctggagatca tagaaccgtg                                               20

<210> SEQ ID NO 26
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 26
acaacagcac tgttggacct                                               20

<210> SEQ ID NO 27
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
```

```
<222> LOCATION: (1)..(20)

<400> SEQUENCE: 27
atgcaatgca agcctgagct                                              20

<210> SEQ ID NO 28
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 28
gctgcctgac tgagacttta                                              20

<210> SEQ ID NO 29
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 29 cttttcctg agcctctata                                               20

<210> SEQ ID NO 30
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 30
aggtccaaca gtgctgttgt                                              20

<210> SEQ ID NO 31
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 31
taaagtctca gtcaggcagc                                              20

<210> SEQ ID NO 32
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(19)

<400> SEQUENCE: 32
```

```
ctctctgctc caaaggcga                                                    19

<210> SEQ ID NO 33
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(18)

<400> SEQUENCE: 33
tgagccactg ttgtcacg                                                     18
```